United States Patent
Treadway

(10) Patent No.: US 6,867,184 B2
(45) Date of Patent: Mar. 15, 2005

(54) METHODS OF TREATING DIABETIC CARDIOMYOPATHY USING GLYCOGEN PHOSPHORYLASE INHIBITORS

(75) Inventor: Judith L. Treadway, Mystic, CT (US)

(73) Assignee: Pfizer, Inc., New York, NY (US)

( * ) Notice: Subject to any disclaimer, the term of this patent is extended or adjusted under 35 U.S.C. 154(b) by 43 days.

(21) Appl. No.: 09/767,633

(22) Filed: Jan. 23, 2001

(65) Prior Publication Data

US 2001/0046958 A1 Nov. 29, 2001

Related U.S. Application Data

(60) Provisional application No. 60/177,770, filed on Jan. 24, 2000.

(51) Int. Cl.$^7$ ............................................. A61K 38/28
(52) U.S. Cl. ......................... 514/4; 514/4; 514/252.14; 514/253; 514/323; 514/330; 514/18; 514/415; 540/295
(58) Field of Search ............................... 514/4, 252.14, 514/253, 323, 330, 18, 415; 540/295

(56) References Cited

U.S. PATENT DOCUMENTS

| | | | |
|---|---|---|---|
| 4,786,641 A | | 11/1988 | Goldmann et al. |
| 5,990,111 A | | 11/1999 | Johnson |
| 5,998,463 A | | 12/1999 | Hulin et al. |
| 6,277,877 B1 | * | 8/2001 | Hoover et al. |
| 6,294,538 B1 | * | 9/2001 | Mylari |

FOREIGN PATENT DOCUMENTS

| | | |
|---|---|---|
| EP | 0846464 | 12/1997 |
| EP | 0884050 | 12/1998 |
| EP | 0 978 279 A1 | 2/2000 |
| EP | 1 088 824 A2 | 4/2001 |
| WO | WO9524391 | 9/1995 |
| WO | WO9639384 | 12/1996 |
| WO | WO9639385 | 12/1996 |
| WO | WO9709040 | 3/1997 |
| WO | WO9731901 | 9/1997 |
| WO | WO0880964 | 5/1998 |
| WO | WO9840353 | 9/1998 |
| WO | WO9850359 | 11/1998 |
| WO | WO9926659 | 6/1999 |
| WO | WO 01/68055 | 9/2001 |
| WO | WO 01/68092 | 9/2001 |
| WO | WO 02/20530 | 3/2002 |

OTHER PUBLICATIONS

Bell, David S. H., *Diabetic Cardiomyopathy: A unique entity or a complication of coronary artery disease?*, Diabetes Care, vol. 18, No. 5, 708–714, May 1995.

Fein, Frederick S., et al., *Diabetic Cardiomyopathy*, Cardiovascular Drugs and Therapy, 1994; 8:65–73.

Hoover, Dennis J., et al., *Indole–2–carboxamide Inhibitors of Human Liver Glycogen Phosphorylase*, American Chemical Society, 1998, 41, 2934–2938.

Martin, et al., "Discovery of a human liver glycogen phosphorylase inhibitor that lowers blood glucose in vivo", *Proc. Natl. Acad. Sci.*, 95:1776–1781 (1998).

European Search Report, Application No. 01 300 575.6–2123, dated Dec. 19, 2003.

* cited by examiner

Primary Examiner—Christopher R. Tate
Assistant Examiner—B. Dell Chism
(74) Attorney, Agent, or Firm—Mark J. Cohen; Gregg C. Benson; Todd M. Crissey

(57) ABSTRACT

The present invention provides methods of treating diabetic cardiomyopathy, the methods comprising administering to a patient having or at risk of having diabetic cardiomyopathy a therapeutically effective amount of a glycogen phosphorylase inhibitor. The present invention also provides methods of treating diabetic cardiomyopathy, the methods comprising administering to a patient having 1) diabetes and 2) having cardiovascular disease, ischemic heart disease, congestive heart failure, congestive heart failure but not having coronary arteriosclerosis, hypertension, diastolic blood pressure abnormalities, microvascular diabetic complications, abnormal left ventricular function, myocardial fibrosis, abnormal cardiac function, pulmonary congestion, small vessel disease, small vessel disease without atherosclerotic cardiovascular disease or luminal narrowing, coagulopathy, cardiac contusion, or having had or at risk of having a myocardial infarction a therapeutically effective amount of a glycogen phosphorylase inhibitor.

10 Claims, No Drawings

METHODS OF TREATING DIABETIC CARDIOMYOPATHY USING GLYCOGEN PHOSPHORYLASE INHIBITORS

CROSS-REFERENCE TO RELATED APPLICATION

This application claims priority of U.S. application No. 60/177,770, filed Jan. 24, 2000.

FIELD OF THE INVENTION

The present invention relates to methods of treating diabetic cardiomyopathy, the methods comprising administering to a patient having or at risk of having diabetic cardiomyopathy a therapeutically effective amount of a glycogen phosphorylase inhibitor. The present invention also relates to methods of treating diabetic cardiomyopathy, the methods comprising administering to a patient having 1) diabetes and 2) having cardiovascular disease, ischemic heart disease, congestive heart failure, congestive heart failure but not having coronary arteriosclerosis, hypertension, diastolic blood pressure abnormalities, microvascular diabetic complications, abnormal left ventricular function, myocardial fibrosis, abnormal cardiac function, pulmonary congestion, small vessel disease, small vessel disease without atherosclerotic cardiovascular disease or luminal narrowing, coagulopathy, cardiac contusion, or having had or at risk of having a myocardial infarction a therapeutically effective amount of a glycogen phosphorylase inhibitor.

BACKGROUND OF THE INVENTION

Diabetic cardiomyopathy, a disease of the heart muscle (myocardium), is considered a distinct medical entity from either diabetes or cardiovascular disease. Diabetic cardiomyopathy occurs in patients having insulin dependent diabetes mellitus (Type 1) and in patients having non-insulin dependent diabetes mellitus (Type 2). Diabetic cardiomyopathy clinically expresses itself as congestive heart failure (CHF) and left ventricular hypertrophy. Diabetic cardiomyopathy is also associated with increased morbidity and mortality. Pathologically, diabetic cardiomyopathy is characterized by myocellular hypertrophy, interstitial fibrosis, increased myocardial lipid deposition, and varying degrees of small vessel disease. Diabetic cardiomyopathy differs from ischemic cardiomyopathy because the diseased myocardium and resultant CHF can occur in the absence of frank coronary atherosclerosis or luminal narrowing. This suggests that the primary metabolic defects related to hyperglycemia that exist in the myocardial tissue and/or in the coronary microcirculation itself are responsible for the diseased state and loss of myocardial function in diabetics. Co-existent hypertension, microvascular complications, impaired fibrinolysis, atherosclerotic cardiovascular disease, and/or myocardial ischemia, which frequently occur in diabetic patients, compound the severity of the underlying diabetic cardiomyopathy. These co-morbidities can lower the threshold for decompensated heart failure, pulmonary edema, and arrhythmias, which can result in the death of the patient.

Diabetic cardiomyopathy can in part explain the increased mortality and morbidity seen in diabetic patients following myocardial infarction or certain cardiovascular interventions, such as coronary artery bypass graft surgery or angioplasty. The microvascular diseases associated with diabetes, e.g. thickened arterial intima (arteriolar hyalinization), microaneurisyms of myocardial arterioles, increased capillary basement membrane thickening, and abnormalities in endothelial metabolism, as well as an impaired fibrinolysis, can contribute to compromised regional blood flow in the heart, resulting in "non-obstructive" ischemia and injury.

Diabetic cardiomyopathy is associated with mechanical dysfunction of the heart. The hypertrophied fibrotic myocardium has reduced compliance, leading to diastolic dysfunction and an elevated left ventricular filling pressure. Progression of the cardiomyopathic process may ultimately result in impairments in myocardial contraction and systolic dysfunction. A reduced stroke volume, low ejection fraction, and impaired cardiac reserve will cause a further rise in left ventricular filling pressures. This may result in fulminant heart failure. This pathophysiology can be reproduced and studied in animal models of diabetic cardiomyopathy.

The underlying cause of diabetic cardiomyopathy appears to be related to hyperglycemia and insulin resistance. The condition is exacerbated by co-existing hypertension. Hyperglycemia causes "glucose toxicity," the exact nature of which is unknown, but may include abnormal myocardial carbohydrate, lipid, and adenine nucleotide metabolism, altered tissue oxygen demand, excess protein and tissue glycosylation, formation of damaging advanced glycation end-products, stimulation of smooth muscle proliferation, increased adhesiveness and aggregation of platelets, and increased production of PAI-1, among other things. These hyperglycemia-associated perturbations contribute to myocardial biochemical changes (e.g. defective cellular metabolism, calcium transport, excess collagen formation) that are observed in the diseased state of the myocardium in diabetics.

The major cause of morbidity and mortality in the diabetic population is cardiovascular disease (CVD). Coronary heart disease (CHD), also referred to as coronary artery disease (CAD), the major cause of myocardial infarction and stroke, and peripheral vascular disease (PVD) are all manifestations of CVD. It is well recognized that diabetics have increased risk of mortality from CVD, which has been primarily attributed to the hyperglycemia associated with their disease, independent of other associated co-morbidities, such as obesity, hypertension, atherosclerosis, and dyslipidemia. The independent risk due to hyperglycemia is often difficult to distinguish in some diabetics, because they also usually possess several of the other co-morbidities mentioned above. Further, their hyperglycemia can exacerbate the severity of the other co-morbidities, leading to interactive effects. Nonetheless, several studies have identified hyperglycemia as a strong independent risk factor even in diabetics with other significant risk factors present. Hyperglycemia is a prime candidate for causing this excess risk, and contributing to the high morbidity and mortality due to CVD in people with diabetes because hyperglycemia causes glucose toxicity. Agents that can reduce glucose toxicity may have beneficial effects on the manifestations of chronic cardiomyopathy, but also may provide more immediate cardioprotection.

Pharmacological cardioprotection can be defined as the use of an agent to protect the myocardium from ischemic or reperfusion injury. The pharmacological agent may, for example, protect heart cells from damage, necrosis, or apoptosis during ischemic or reperfusion injury by mimicking ischemic preconditioning, which is a naturally occurring, physiologic phenomenon that provides endogenous cardioprotection. The cardioprotective effects, depending on the agent used, may be both immediate (minutes-hours) or delayed (24–72 hours) post-ischemia. Cardioprotective agents may be useful for reducing both perioperative and non-perioperative ischemic injury. Cardioprotective agents may be especially useful in diabetics who are at increased risk of both acute myocardial infarction and chronic cardiomyopathies.

U.S. Pat. No. 5,990,111 discloses the treatment of diabetic cardiomyopathy using an aldose reductase inhibitor.

SUMMARY OF THE INVENTION

The present invention provides methods of treating diabetic cardiomyopathy, the methods comprising administering to a patient having or at risk of having diabetic cardiomyopathy a therapeutically effective amount of a glycogen phosphorylase inhibitor.

In a preferred embodiment of the method, the glycogen phosphorylase inhibitor is 5-chloro-1H-indole-2-carboxylic acid [(1S)-((R)-hydroxy-dimethylcarbamoyl-methyl)-2-phenyl-ethyl]-amide;

5,6-dichloro-1H-indole-2-carboxylic acid {(1S)-[(R)-hydroxy-(methoxy-methyl-carbamoyl)-methyl]-2-phenyl-ethyl}-amide;

5-chloro-1H-indole-2-carboxylic acid {(1S)-[(R)-hydroxy-(methoxy-methyl-carbamoyl)-methyl]-2-phenyl-ethyl}-amide;

5-chloro-1H-indole-2-carboxylic acid ((1S)-{(R)-hydroxy-[(2-hydroxy-ethyl)-methyl-carbamoyl]-methyl}-2-phenyl-ethyl)-amide;

5-chloro-1H-indole-2-carboxylic acid [(1S)-benzyl-3-((3R,4S)-dihydroxy-pyrrolidin-1-yl)-(2R)-hydroxy-3-oxo-propyl]-amide;

5-chloro-1H-indole-2-carboxylic acid {(1S)-[(R)-hydroxy-(methyl-pyridin-2-yl-carbamoyl)-methyl]-2-phenyl-ethyl}-amide; or 5-chloro-1H-indole-2-carboxylic acid ((1S)-{(R)-hydroxy-[methyl-(2-pyridin-2-yl-ethyl)-carbamoyl]-methyl}-2-phenyl-ethyl)-amide, or a pharmaceutically acceptable salt or prodrug thereof, or a salt of a prodrug.

Also provided are methods of treating diabetic cardiomyopathy, the methods comprising administering to a patient having diabetes and cardiovascular disease a therapeutically effective amount of a glycogen phosphorylase inhibitor.

Also provided are methods of treating diabetic cardiomyopathy, the methods comprising administering to a patient having diabetes and ischemic heart disease a therapeutically effective amount of a glycogen phosphorylase inhibitor.

Also provided are methods of treating diabetic cardiomyopathy, the methods comprising administering to a patient having diabetes and having had or at risk of having a myocardial infarction a therapeutically effective amount of a glycogen phosphorylase inhibitor.

Also provided are methods of treating diabetic cardiomyopathy, the methods comprising administering to a patient having diabetes and congestive heart failure a therapeutically effective amount of a glycogen phosphorylase inhibitor.

Also provided are methods of treating diabetic cardiomyopathy, the methods comprising administering to a patient having diabetes and congestive heart failure, but not having coronary arteriosclerosis, a therapeutically effective amount of a glycogen phosphorylase inhibitor.

Also provided are methods of treating diabetic cardiomyopathy, the methods comprising administering to a patient having diabetes and hypertension a therapeutically effective amount of a glycogen phosphorylase inhibitor.

Also provided are methods of treating diabetic cardiomyopathy, the methods comprising administering to a patient having diabetes and diastolic blood pressure abnormalities a therapeutically effective amount of a glycogen phosphorylase inhibitor.

Also provided are methods of treating diabetic cardiomyopathy, the methods comprising administering to a patient having diabetes and microvascular diabetic complications a therapeutically effective amount of a glycogen phosphorylase inhibitor.

Also provided are methods of treating diabetic cardiomyopathy, the methods comprising administering to a patient having diabetes and abnormal left ventricular function a therapeutically effective amount of a glycogen phosphorylase inhibitor.

Also provided are methods of treating diabetic cardiomyopathy, the methods comprising administering to a patient having diabetes and myocardial fibrosis a therapeutically effective amount of a glycogen phosphorylase inhibitor.

Also provided are methods of treating diabetic cardiomyopathy, the methods comprising administering to a patient having diabetes and abnormal cardiac function a therapeutically effective amount of a glycogen phosphorylase inhibitor.

Also provided are methods of treating diabetic cardiomyopathy, the methods comprising administering to a patient having diabetes and pulmonary congestion a therapeutically effective amount of a glycogen phosphorylase inhibitor.

Also provided are methods treating diabetic cardiomyopathy, the methods comprising administering to a patient having diabetes and small vessel disease a therapeutically effective amount of a glycogen phosphorylase inhibitor.

Also provided are methods of treating diabetic cardiomyopathy, the methods comprising administering to a patient having diabetes and small vessel disease without atherosclerotic cardiovascular disease or luminal narrowing a therapeutically effective amount of a glycogen phosphorylase inhibitor.

Also provided are methods of treating diabetic cardiomyopathy, the methods comprising administering to a patient having diabetes and coagulopathy a therapeutically effective amount of a glycogen phosphorylase inhibitor.

Also provided are methods of treating diabetic cardiomyopathy, the methods comprising administering to a patient having diabetes and cardiac contusion a therapeutically effective amount of a glycogen phosphorylase inhibitor.

Also provided are methods of preventing or decreasing injury to the myocardium, the methods comprising administering to a diabetic patient who is at risk of suffering myocardial ischemia and reperfusion a therapeutically effective amount of a glycogen phosphorylase inhibitor.

In a preferred embodiment of the methods of preventing or decreasing injury to the myocardium, the diabetic patient is at risk of suffering myocardial ischemia and reperfusion as a result of having to undergo a balloon angioplasty.

In another preferred embodiment of the methods of preventing or decreasing injury to the myocardium, the diabetic patient is at risk of suffering myocardial ischemia and reperfusion as a result of having to undergo major non-cardiac surgery.

In another preferred embodiment of the methods of preventing or decreasing injury to the myocardium, the diabetic patient is at risk of suffering myocardial ischemia and reperfusion as a result of having to undergo bypass surgery.

It is noted that in the methods of preventing or decreasing injury to the myocardium, it is preferable if the glycogen phosphorylase is administered prior to suffering myocardial ischemia and reperfusion.

Also provided are methods of preventing or delaying the onset of diabetic cardiomyopathy, the methods comprising administering to a patient newly diagnosed as having diabetes a therapeutically effective amount of a glycogen phosphorylase inhibitor.

Also provided is a method of treating diabetic cardiomyopathy, the method comprising administering to a patient having or at risk of having diabetic cardiomyopathy a therapeutically effective amount of a glycogen phosphorylase inhibitor in combination with an additional compound, the additional compound being useful to treat diabetes, cardiovascular disease, ischemic heart disease, congestive heart failure, hypertension, diastolic blood pressure abnormalities, microvascular diabetic complications, abnormal left ventricular function, myocardial fibrosis, abnormal cardiac function, pulmonary congestion, small vessel disease, coagulopathy, cardiac contusion, or myocardial infarction.

In a preferred embodiment, the additional compound is selected from insulin and insulin analogs; biguanides; α2-antagonists and imidazolines; glitazones; PPAR-gamma agonists; fatty acid oxidation inhibitors; α-glucosidase inhibitors; β-agonists; phosphodiesterase inhibitors; lipid-lowering agents; antiobesity agents; vanadate, vanadium and peroxovanadium complexes; amylin antagonists; glucagon antagonists; gluconeogenesis inhibitors; somatostatin analogs and antagonists; or antilipolytic agents.

In another preferred embodiment, the additional compound is selected from an aldose reductase inhibitor; a sorbitol dehydrogenase inhibitor; a glucocorticoid receptor antagonist; a NHE-1 inhibitor; or a thyromimetic.

DETAILED DESCRIPTION OF THE INVENTION

The present invention provides methods of treating diabetic cardiomyopathy, the methods comprising administering to a patient having or at risk of having diabetic cardiomyopathy a therapeutically effective amount of a glycogen phosphorylase inhibitor. The present invention also provides methods of treating diabetic cardiomyopathy, the methods comprising administering to a patient having 1) diabetes and 2) having cardiovascular disease, ischemic heart disease, congestive heart failure, congestive heart failure but not having coronary arteriosclerosis, hypertension, diastolic blood pressure abnormalities, microvascular diabetic complications, abnormal left ventricular function, myocardial fibrosis, abnormal cardiac function, pulmonary congestion, small vessel disease, small vessel disease without atherosclerotic cardiovascular disease or luminal narrowing, coagulopathy, cardiac contusion, or having had or at risk of having a myocardial infarction, a therapeutically effective amount of a glycogen phosphorylase inhibitor.

In treating diabetic cardiomyopathy, it is important to note that patients having diabetes and having an additional condition or disease such as cardiovascular disease, ischemic heart disease, congestive heart failure, congestive heart failure but not having coronary arteriosclerosis, hypertension, diastolic blood pressure abnormalities, microvascular diabetic complications, abnormal left ventricular function, myocardial fibrosis, abnormal cardiac function, pulmonary congestion, small vessel disease, small vessel disease without atherosclerotic cardiovascular disease or luminal narrowing, coagulopathy, cardiac contusion, or having or at risk of having a myocardial infarction are at particular risk for developing very serious cardiac insufficiencies including death because diabetic cardiomyopathy further adversely affects the patient's heart and cardiovascular system.

The term "therapeutically effective amount" means an amount of a compound or combination of compounds that ameliorates, attenuates, or eliminates one or more symptoms of a particular disease or condition or prevents or delays the onset of one or more symptoms of a particular disease or condition.

The term "patient" means animals, such as dogs, cats, cows, horses, sheep, and humans. Particularly preferred patients are mammals. The term patient includes males and females.

The term "pharmaceutically acceptable" means that the carrier, diluent, excipients, and/or salt must be compatible with the other ingredients of the formulation, and not deleterious to the patient.

The terms "treating", "treat" or "treatment" include preventative (e.g., prophylactic) and palliative treatment.

The phrase "glycogen phosphorylase inhibitor" refers to any substance or any combination of substances that reduces, retards, or eliminates the enzymatic action of glycogen phosphorylase. The currently known enzymatic action of glycogen phosphorylase is the degradation of glycogen by catalysis of the reversible reaction of a glycogen macromolecule and inorganic phosphate to glucose-1-phosphate and a glycogen macromolecule which is one glucosyl residue shorter than the original glycogen macromolecule (forward direction of glycogenolysis). The phrase glycogen phosphorylase inhibitor includes the stereoisomers, pharmaceutically acceptable salts, prodrugs, and pharmaceutically acceptable salts of the prodrugs of the glycogen phosphorylase inhibitor.

The phrase "newly diagnosed as having diabetes" means that the patient has been diagnosed with diabetes, either Type 1 or Type 2, within one year. Preferably, the patient has been diagnosed with diabetes within six months, and more preferably within one month.

The phrase "major non-cardiac surgery" means surgery that is not directed to the heart and requires a stay of at least one day in a hospital or under equivalent observation. Examples of major non-cardiac surgeries include tumor removal, limb amputation, brain surgery, transplant surgery, and the like.

The phrase "cardiovascular disease" means a disease (or diseases) involving or affecting the heart, blood vessels, and/or circulatory system.

The phrase "ischemic heart disease" (also called myocardial ischemia) means inadequate myocardial blood flow (perfusion), or other condition of the heart that results in oxygen deprivation and inadequate removal of metabolites. This includes any condition where there is an imbalance between myocardial oxygen supply and demand.

The phrase "diastolic blood pressure abnormalities" means any condition that results, under testing conditions described by the American Heart Association (AHA), in a diastolic blood pressure value of greater than or equal to 90 mm Hg (American Heart Association's Sixth Report of the Joint National Committee on Detection, Evaluation, and Treatment of High Blood Pressure, NIH publication). It is noted that diastolic blood pressure abnormalities can also lead to systolic blood pressure abnormalities (dysfunction), by contributing to a condition of the heart whereby, for example, there is reduced capacity to increase ejection fraction during exertion. It is also noted that the 90 mm Hg number currently set by the AHA may be changed in the future. The meaning of the phrase diastolic blood pressure abnormalities is intended to track the criteria provided by the AHA.

The phrase "microvascular diabetic complications" means diabetic retinopathy, nephropathy, and neuropathy, which can lead to renal failure, peripheral arterial disease, or limb amputation.

The phrase "abnormal left ventricular function" means a condition of the heart, blood vessels, and/or circulatory system that results in reduced or abnormal left ventricular (LV) functioning, as detected, for example, via echocardiography or radionuclide ventriculography. Contributing factors to abnormal LV function include increased heart wall stiffness, reduced LV compliance, and/or increased peripheral vascular resistance. The abnormal functioning of the LV can manifest, for example, as altered myocardial contractility (decreased dP/dT, prolonged duration of contraction, and delayed relaxation), LV asynergy, reduced peak diastolic filling rate, and/or abnormal LV ejection fraction, under either normal or exercise test conditions. LV dysfunction is also any condition of the heart, blood vessels, and/or circulatory system that leads to the left ventricle having abnormal relaxation and reduced compliance associated with slow and incomplete cardiac filling.

The phrase "abnormal cardiac function" means any diseased state or abnormal condition of the heart that prevents or reduces normal cardiac function, as defined by normal heart rate, normal blood pressure, and normal ECG readings. Most relevant to diabetic cardiomyopathy is the abnormal functioning of the myocardium that leads to blood pressure abnormalities, primarily elevated diastolic blood pressure, which may in turn lead to elevated systolic blood pressure and/or systolic dysfunction (e.g. reduced ejection fraction during exertion). Normal blood pressure is nominally defined as <140 systolic and <90 diastolic mm Hg by the current AHA guidelines (American Heart Association's Sixth Report of the Joint National Committee on Detection, Evaluation, and Treatment of High Blood Pressure, NIH publication, 1997). It is also noted that the normal blood pressure criteria currently set by the AHA may be changed in the future. The meaning of the phrase abnormal cardiac function is intended to track the criteria provided by the AHA.

The phrase "small vessel disease" (also referred to as microangiopathy) means a diseased condition of the intramyocardial arteries, arterioles, and vessels distal to the arterioles, namely capillaries, venules, and small veins. Microangiopathy may be characterized by aneurysm, microaneurysms, degeneration, necrosis (e.g. myocytolytic necrosis), spasm, hyperreactivity, leakiness, interstitial edema, perivasacular fibrosis, sclerosis, replacement scarring, tortuosity, focal constrictions, increased capillary basement membrane thickening, abnormalities in endothelial metabolism, or damage caused by impaired fibrinolysis.

The phrase "atherosclerotic cardiovascular disease" means a cardiovascular disease that is associated with or secondary to an atherosclerotic condition, e.g. a diseased state of the arteries characterized by an accumulation of intimal smooth muscle cells, accumulation of macrophages and T-lymphocytes, formation of large amounts of connective tissue matrix, and accumulation of lipid, primarily in the form of cholesterol or cholesterol esters within the cells and the surrounding connective tissue, and accumulation of necrotic debris.

The phrase "microvascular disease" means a diseased condition of the arterioles and/or the vessels distal to the arterioles, including, but not limited to, the resistance vessels. Microvascular disease may be characterized by an unevenly distributed thickening (or hyalinization) of the intima of small arterioles, primarily due to the accumulation of type IV collagen in the basement membrane, or microaneurisyms of the arterioles, which compromises the extent of the maximal arteriolar dilation that can be achieved and impairs the delivery of nutrients and hormones to the tissues, and/or to remove waste. The vasculature distal to the arterioles may also be affected, such as by increased capillary basement membrane thickening, abnormalities in endothelial metabolism, or via impaired fibrinolysis, also resulting in reduced delivery of nutrients and hormones to the tissues, and/or waste removal. Microvascular disease can result in microvascular diabetic complications.

The present invention contemplates the use of any compound that is a glycogen phosphorylase inhibitor. Examples of some useful glycogen phosphorylase inhibitors are set forth below.

One group of glycogen phosphorylase inhibitors that can be used to treat diabetic cardiomyopathy includes compounds of Formula A:

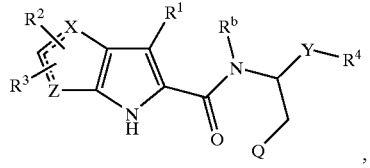

A a stereoisomer, pharmaceutically acceptable salt or prodrug thereof, or a pharmaceutically acceptable salt of the prodrug, wherein Q is aryl, substituted aryl, heteroaryl, or substituted heteroaryl;

each Z and X are independently (C, CH or $CH_2$), N, O or S;

$X^1$ is $NR^a$, —$CH_2$—, O or S;

each — is independently a bond or is absent, provided that both — are not simultaneously bonds;

$R^1$ is hydrogen, halogen, —$OC_1$–$C_8$alkyl, —$SC_1$–$C_8$alkyl, —$C_1$–$C_8$alkyl, —$CF_3$, —$NH_2$, —$NHC_1$–$C_8$alkyl, —$N(C_1$–$C_8$alkyl$)_2$, —$NO_2$, —CN, —$CO_2$H, —$CO_2C_1$–$C_8$alkyl, —$C_2$–$C_8$alkenyl, or —$C_2$–$C_8$alkynyl; each $R^a$ and $R^b$ is independently hydrogen or —$C_1$–$C_8$alkyl;

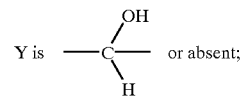

Y is —C— or absent;

$R^2$ and $R^3$ are independently hydrogen, halogen, —$C_1$–$C_8$alkyl, —CN, —C≡C—Si$(CH_3)_3$, —$OC_1$–$C_8$alkyl, —$SC_1$–$C_8$alkyl, —$CF_3$, —$NH_2$, —$NHC_1$–$C_8$alkyl, —$N(C_1$–$C_8$alkyl$)_2$, —$NO_2$, —$CO_2$H, —$CO_2C_1$–$C_8$alkyl, —$C_2$–$C_8$alkenyl, or —$C_2$–$C_8$alkynyl, or $R^2$ and $R^3$ together with the atoms on the ring to which they are attached form a five or six membered ring containing from 0 to 3 heteroatoms and from 0 to 2 double bonds;

$R^4$ is —C(=O)—A;

A is —$NR^dR^d$, —$NR^aCH_2CH_2OR^a$,

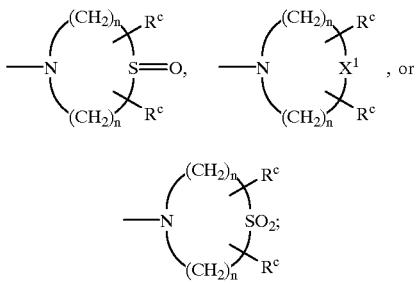, or each $R^d$ is independently hydrogen, $C_1$–$C_8$alkyl, $C_1$–$C_8$alkoxy, aryl, substituted aryl, heteroaryl, or substituted heteroaryl;

each $R^c$ is independently hydrogen, —C(=O)$OR^a$, —$OR^a$, —$SR^a$, or —$NR^aR^a$; and each n is independently 1–3.

Preferred examples of glycogen phosphorylase inhibitors of Formula A include 6H-thieno[2,3-b]pyrrole-5-carboxylic acid [(1S)-benzyl-3-((3R,4S)-dihydroxy-pyrrolidin-1-yl)-(2R)-hydroxy-3-oxo-propyl]-amide;

2-bromo-6H-thieno[2,3-b]pyrrole-5-carboxylic acid [(1S)-benzyl-3-((3R,4S)-dihydroxy-pyrrolidin-1-yl)-(2R)-hydroxy-3-oxo-propyl]-amide;

2-methyl-6H-thieno[2,3-b]pyrrole-5-carboxylic acid [(1S)-benzyl-3-((3R,4S)-dihydroxy-pyrrolidin-1-yl)-(2R)-hydroxy-3-oxo-propyl]-amide;

(±)-2-methyl-6H-thieno[2,3-b]pyrrole-5-carboxylic acid [1-benzyl-2-((3R,4S)-dihydroxy-pyrrolidin-1-yl)-2-oxo-ethyl]-amide;

2-bromo-6H-thieno[2,3-b]pyrrole-5-carboxylic acid [(1S)-benzyl-2-((3R,4S)-dihydroxy-pyrrolidin-1-yl)-2-oxo-ethyl]-amide;

2-chloro-6H-thieno[2,3-b]pyrrole-5-carboxylic acid [(1S)-benzyl-3-((3R,4S)-dihydroxy-pyrrolidin-1-yl)-(2R)-hydroxy-3-oxo-propyl]-amide;

2-chloro-6H-thieno[2,3-b]pyrrole-5-carboxylic acid [(1S)-benzyl-2-((3R,4S)-dihydroxy-pyrrolidin-1-yl)-2-oxo-ethyl]-amide;

2,4-dichloro-6H-thieno[2,3-b]pyrrole-5-carboxylic acid [(1S)-benzyl-3-((3R,4S)-dihydroxy-pyrrolidin-1-yl)-(2R)-hydroxy-3-oxo-propyl]-amide;

(±)-4H-thieno[3,2-b]pyrrole-5-carboxylic acid [1-benzyl-2-((3R,4S)-dihydroxy-pyrrolidin-1-yl)-2-oxo-ethyl]-amide;

2-bromo-4H-thieno[3,2-b]pyrrole-5-carboxylic acid [(1S)-benzyl-3-((3R,4S)-dihydroxy-pyrrolidin-1-yl)-(2R)-hydroxy-3-oxo-propyl]-amide;

4H-thieno[3,2-b]pyrrole-5-carboxylic acid [(1S)-benzyl-3-((3R,4S)-dihydroxy-pyrrolidin-1-yl)-(2R)-hydroxy-3-oxo-propyl]-amide;

(±)-2-bromo-4H-furo[3,2-b]pyrrole-5-carboxylic acid [1-benzyl-2-((3R,4S)-dihydroxy-pyrrolidin-1-yl)-2-oxo-ethyl]-amide;

2-bromo-4H-furo[3,2-b]pyrrole-5-carboxylic acid [(1S)-benzyl-3-((3R,4S)-dihydroxy-pyrrolidin-1-yl)-(2R)-hydroxy-3-oxo-propyl]-amide;

6H-thieno[2,3-b]pyrrole-5-carboxylic acid [(1S)-benzyl-2-((3R,4S)-dihydroxy-pyrrolidin-1-yl)-2-oxo-ethyl]-amide;

2-bromo-4H-thieno[3,2-b]pyrrole-5-carboxylic acid [(1S)-benzyl-2-((3R,4S)-dihydroxy-pyrrolidin-1-yl)-2-oxo-ethyl]-amide;

2-methyl-4H-thieno[3,2-b]pyrrole-5-carboxylic acid [(1S)-benzyl-2-((3R,4S)-dihydroxy-pyrrolidin-1-yl)-2-oxo-ethyl]-amide;

2,4-dichloro-6H-thieno[2,3-b]pyrrole-5-carboxylic acid [(1S)-benzyl-2-((3R,4S)-dihydroxy-pyrrolidin-1-yl)-2-oxo-ethyl]-amide;

2-cyano-6H-thieno[2,3-b]pyrrole-5-carboxylic acid [(1S)-benzyl-2-(3-hydroxy-azetidin-1-yl)-2-oxo-ethyl]-amide;

2-chloro-6H-thieno[2,3-b]pyrrole-5-carboxylic acid [(1S)-benzyl-2-morpholin-4-yl-2-oxo-ethyl]-amide;

2-chloro-6H-thieno[2,3-b]pyrrole-5-carboxylic acid [(1S)-dimethylcarbamoyl-2-phenyl-ethyl]-amide;

2-chloro-6H-thieno[2,3-b]pyrrole-5-carboxylic acid [(1S)-benzyl-2-(1,1-dioxo-1-thiazolidin-3-yl)-2-oxo-ethyl]-amide;

1-{(2S)-[(2-chloro-6H-thieno[2,3-b]pyrrole-5-carbonyl)-amino]-3-phenyl-propionyl}-piperidine-4-carboxylic acid ethyl ester;

2-bromo-6H-thieno[2,3-b]pyrrole-5-carboxylic acid [(1S)-benzyl-2-(3-hydroxy-azetidin-1-yl)-2-oxo-ethyl]-amide;

2-methyl-4H-furo[3,2-b]pyrrole-5-carboxylic acid [(1S)-benzyl-2-((3R,4S)-dihydroxy-pyrrolidin-1-yl)-2-oxo-ethyl]-amide;

2-trimethylsilanylethynyl-6H-thieno[2,3-b]pyrrole-5-carboxylic acid [(1S)-benzyl-2-(3-hydroxy-azetidin-1-yl)-2-oxo-ethyl]-amide;

2-ethynyl-6H-thieno[2,3-b]pyrrole-5-carboxylic acid [(1S)-benzyl-2-(3-hydroxy-azetidin-1-yl)-2-oxo-ethyl]-amide;

2-fluoro-4H-thieno[3,2-b]pyrrole-5-carboxylic acid [(1S)-benzyl-2-((3R,4S)-dihydroxy-pyrrolidin-1-yl)-2-oxo-ethyl]-amide;

2-cyano-4H-furo[3,2-b]pyrrole-5-carboxylic acid [(1S)-benzyl-2-(3-hydroxy-azetidin-1-yl)-2-oxo-ethyl]-amide;

2-chloro-4H-furo[3,2-b]pyrrole-5-carboxylic acid [(1S)-benzyl-2-((3R,4S)-dihydroxy-pyrrolidin-1-yl)-2-oxo-ethyl]-amide;

2-chloro-4H-furo[3,2-b]pyrrole-5-carboxylic acid [(1S)-benzyl-3-((3R,4S)-dihydroxy-pyrrolidin-1-yl)-(2R)-hydroxy-3-oxo-propyl]-amide;

1-{(2S)-[(2-chloro-6H-thieno[2,3-b]pyrrole-5-carbonyl)-amino]-3-phenyl-propionyl}-piperidine-4-carboxylic acid;

3-chloro-4H-thieno[3,2-b]pyrrole-5-carboxylic acid [(1S)-benzyl-2-((3R,4S)-dihydroxy-pyrrolidin-1-yl)-2-oxo-ethyl]-amide;

3-chloro-4H-thieno[3,2-b]pyrrole-5-carboxylic acid [(1S)-benzyl-3-((3R,4S)-dihydroxy-pyrrolidin-1-yl)-(2R)-hydroxy-3-oxo-propyl]-amide;

3-bromo-4H-thieno[3,2-b]pyrrole-5-carboxylic acid [(1S)-benzyl-2-((3R,4S)-dihydroxy-pyrrolidin-1-yl)-2-oxo-ethyl]-amide;

3-bromo-4H-thieno[3,2-b]pyrrole-5-carboxylic acid [(1S)-benzyl-3-((3R,4S)-dihydroxy-pyrrolidin-1-yl)-(2R)-hydroxy-3-oxo-propyl]-amide;

2-chloro-4H-thieno[3,2-b]pyrrole-5-carboxylic acid [(1S)-benzyl-3-((3R,4S)-dihydroxy-pyrrolidin-1-yl)-(2R)-hydroxy-3-oxo-propyl]-amide;

2-chloro-4H-thieno[3,2-b]pyrrole-5-carboxylic acid [(1S)-benzyl-2-((3R,4S)-dihydroxy-pyrrolidin-1-yl)-2-oxo-ethyl]-amide;

3-methyl-4H-thieno[3,2-b]pyrrole-5-carboxylic acid [(1S)-benzyl-2-((3R,4S)-dihydroxy-pyrrolidin-1-yl)-2-oxo-ethyl]-amide;

3-methyl-4H-thieno[3,2-b]pyrrole-5-carboxylic acid [(1S)-benzyl-3-((3R,4S)-dihydroxy-pyrrolidin-1-yl)-(2R)-hydroxy-3-oxo-propyl]-amide;

2-cyano-4H-thieno[3,2-b]pyrrole-5-carboxylic acid [(1S)-benzyl-2-((3R,4S)-dihydroxy-pyrrolidin-1-yl)-2-oxo-ethyl]-amide;

2-cyano-4H-furo[3,2-b]pyrrole-5-carboxylic acid [(1S)-benzyl-3-((3R,4S)-dihydroxy-pyrrolidin-1-yl)-(2R)-hydroxy-3-oxo-propyl]-amide;

3-bromo-4H-furo[3,2-b]pyrrole-5-carboxylic acid [(1S)-benzyl-2-((3R,4S)-dihydroxy-pyrrolidin-1-yl)-2-oxo-ethyl]-amide;

3-bromo-4H-furo[3,2-b]pyrrole-5-carboxylic acid [(1S)-benzyl-3-((3R,4S)-dihydroxy-pyrrolidin-1-yl)-(2R)-hydroxy-3-oxo-propyl]-amide;

4H-1,7-dithia-4-aza-cyclopenta[a]pentalene-5-carboxylic acid [(1S)-benzyl-3-((3R,4S)-dihydroxy-pyrrolidin-1-yl)-(2R)-hydroxy-3-oxo-propyl]-amide;

4H-1,7-dithia-4-aza-cyclopenta[a]pentalene-5-carboxylic acid [(1S)-benzyl-2-((3R,4S)-dihydroxy-pyrrolidin-1-yl)-2-oxo-ethyl]-amide;

2-chloro-3-methyl-4H-thieno[3,2-b]pyrrole-5-carboxylic acid [(1S)-benzyl-2-((3R,4S)-dihydroxy-pyrrolidin-1-yl)-2-oxo-ethyl]-amide;

2-chloro-3-methyl-4H-thieno[3,2-b]pyrrole-5-carboxylic acid [(1S)-benzyl-3-((3R,4S)-dihydroxy-pyrrolidin-1-yl)-(2R)-3-oxo-propyl]-amide;

2-methylsulfanyl-4H-thieno[3,2-b]pyrrole-5-carboxylic acid [(1S)-benzyl-2-((3R,4S)-dihydroxy-pyrrolidin-1-yl)-2-oxo-ethyl]-amide;

2-Bromo-4H-thieno[3,2-b]pyrrole-5-carboxylic acid [(1S)-benzyl-2-(3-hydroxy-azetidin-1-yl)-2-oxo-ethyl]-amide;

2-Bromo-4H-thieno[3,2-b]pyrrole-5-carboxylic acid [(1S)-benzyl-2-(1,1-dioxo-1-thiazolidin-3-yl)-2-oxo-ethyl]-amide;

2-Bromo-4H-thieno[3,2-b]pyrrole-5-carboxylic acid [(1S)-benzyl-2-morpholin-4-yl-2-oxo-ethyl]-amide;

2-bromo-4H-thieno[3,2-b]pyrrole-5-carboxylic acid [(1S)-benzyl-2-((3S,4S)-dihydroxy-pyrrolidin-1-yl)-2-oxo-ethyl]-amide;

2-bromo-4H-thieno[3,2-b]pyrrole-5-carboxylic acid [(1S)-benzyl-2-((3R,4R)-dihydroxy-pyrrolidin-1-yl)-2-oxo-ethyl]-amide; and 2-bromo-4H-thieno[3,2-b]pyrrole-5-carboxylic acid [(1S)-benzyl-2-(4-hydroxy-piperidin-1-yl)-2-oxo-ethyl]-amide, and the stereoisomers, pharmaceutically acceptable salts and prodrugs of the compounds, and the pharmaceutically acceptable salts of the prodrugs.

Methods for making the above recited glycogen phosphorylase inhibitors of Formula A can be found in U.S. provisional patent application No. 60/157,148, filed Sep. 30, 1999.

Commonly assigned PCT published applications WO 96/39384 and WO 96/39385 disclose glycogen phosphorylase inhibitors of Formulas I and IA below that can be used to treat diabetic cardiomyopathy in accordance with the present invention.

One group of glycogen phosphorylase inhibitors that can be used in the present invention includes compounds of Formula I

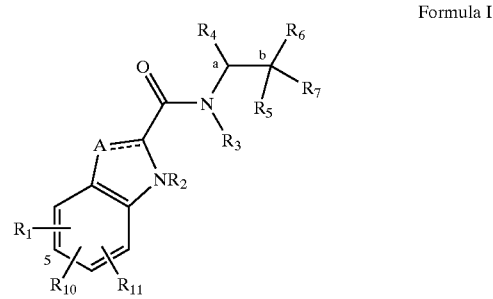

Formula I and the pharmaceutically acceptable salts and prodrugs thereof
wherein
the dotted line (—) is an optional bond;
A is —C(H)=, —C((C$_1$–C$_4$)alkyl)= or —C(halo)= when the dotted line (—) is a bond, or A is methylene or —CH((C$_1$–C$_4$)alkyl)- when the dotted line (—) is not a bond;
$R_1$, $R_{10}$ or $R_{11}$ are each independently H, halo, 4-, 6- or 7-nitro, cyano, (C$_1$–C$_4$)alkyl, (C$_1$–C$_4$)alkoxy, fluoromethyl, difluoromethyl or trifluoromethyl;
$R_2$ is H;
$R_3$ is H or (C$_1$–C$_5$)alkyl;
$R_4$ is H, methyl, ethyl, n-propyl, hydroxy(C$_1$–C$_3$)alkyl, (C$_1$–C$_3$)alkoxy(C$_1$–C$_3$)alkyl, phenyl(C$_1$–C$_4$)alkyl, phenylhydroxy(C$_1$–C$_4$)alkyl, phenyl(C$_1$–C$_4$)alkoxy(C$_1$–C$_4$)alkyl, thien-2- or -3-yl(C$_1$–C$_4$)alkyl or fur-2- or -3-yl(C$_1$–C$_4$)alkyl wherein said $R_4$ rings are mono-, di- or tri-substituted independently on carbon with H, halo, (C$_1$–C$_4$)alkyl, (C$_1$–C$_4$)alkoxy, trifluoromethyl, hydroxy, amino or cyano; or
$R_4$ is pyrid-2-, -3- or 4-yl(C$_1$–C$_4$)alkyl, thiazol-2-, 4- or -5-yl(C$_1$–C$_4$)alkyl, imidazol-1-, -2-, -4- or -5-yl (C$_1$–C$_4$)alkyl, pyrrol-2- or -3-yl(C$_1$–C$_4$)alkyl, oxazol-2-, -4- or -5-yl-(C$_1$–C$_4$)alkyl, pyrazol-3-, -4- or -5-yl (C$_1$–C$_4$)alkyl, isoxazol-3-, -4- or -5-yl(C$_1$–C$_4$)alkyl, isothiazol-3-, -4- or -5-yl(C$_1$–C$_4$)alkyl, pyridazin-3- or -4-yl-(C$_1$–C$_4$)alkyl, pyrimidin-2-, -4-, -5- or -6-yl (C$_1$–C$_4$)alkyl, pyrazin-2- or -3-yl(C$_1$–C$_4$)alkyl or 1,3,5-triazin-2-yl(C$_1$–C$_4$)alkyl, wherein said preceding $R_4$ heterocycles are optionally mono- or di-substituted independently with halo, trifluoromethyl, (C$_1$–C$_4$) alkyl, (C$_1$–C$_4$)alkoxy, amino or hydroxy and said mono-or di-substituents are bonded to carbon;
$R_5$ is H, hydroxy, fluoro, (C$_1$–C$_5$)alkyl, (C$_1$–C$_5$)alkoxy, (C$_1$–C$_6$)alkanoyl, amino(C$_1$–C$_4$)alkoxy, mono-N— or di-N,N—(C$_1$–C$_4$)alkylamino(C$_1$–C$_4$)alkoxy, carboxy (C$_1$–C$_4$)alkoxy, (C$_1$–C$_5$)alkoxy-carbonyl(C$_1$–C$_4$) alkoxy, benzyloxycarbonyl(C$_1$–C$_4$)alkoxy, or carbonyloxy wherein said carbonyloxy is carbon-carbon linked with phenyl, thiazolyl, imidazolyl, 1H-indolyl, furyl, pyrrolyl, oxazolyl, pyrazolyl, isoxazolyl, isothiazolyl, pyridazinyl, pyrimidinyl, pyrazinyl or 1,3,5-triazinyl and wherein said preceding $R_5$ rings are optionally mono-substituted with halo, (C$_1$–C$_4$)alkyl, (C$_1$–C$_4$) alkoxy, hydroxy, amino or trifluoromethyl and said mono-substituents are bonded to carbon;
$R_7$ is H, fluoro or (C$_1$–C$_5$)alkyl; or
$R_5$ and $R_7$ can be taken together to be oxo;

$R_6$ is carboxy, $(C_1-C_8)$alkoxycarbonyl, $C(O)NR_8R_9$ or $C(O)R_{12}$, wherein $R_8$ is H, $(C_1-C_3)$alkyl, hydroxy or $(C_1-C_3)$alkoxy; and $R_9$ is H, $(C_1-C_8)$alkyl, hydroxy, $(C_1-C_8)$alkoxy, methylene-perfluorinated$(C_1-C_8)$alkyl, phenyl, pyridyl, thienyl, furyl, pyrrolyl, pyrrolidinyl, oxazolyl, thiazolyl, imidazolyl, pyrazolyl, pyrazolinyl, pyrazolidinyl, isoxazolyl, isothiazolyl, pyranyl, piperidinyl, morpholinyl, pyridazinyl, pyrimidinyl, pyrazinyl, piperazinyl or 1,3,5-triazinyl wherein said preceding $R_9$ rings are carbon-nitrogen linked; or $R_9$ is mono-, di- or tri-substituted $(C_1-C_5)$alkyl, wherein said substituents are independently H, hydroxy, amino, mono-N— or di-N,N—$(C_1-C_5)$alkylamino; or $R_9$ is mono- or di-substituted $(C_1-C_5)$alkyl, wherein said substituents are independently phenyl, pyridyl, furyl, pyrrolyl, pyrrolidinyl, oxazolyl, thiazolyl, imidazolyl, pyrazolyl, pyrazolinyl, pyrazolidinyl, isoxazolyl, isothiazolyl, pyranyl, pyridinyl, piperidinyl, morpholinyl, pyridazinyl, pyrimidinyl, pyrazinyl, piperazinyl or 1,3,5-triazinyl wherein the nonaromatic nitrogen-containing $R_9$ rings are optionally mono-substituted on nitrogen with $(C_1-C_6)$ alkyl, benzyl, benzoyl or $(C_1-C_6)$alkoxycarbonyl and wherein the $R_9$ rings are optionally mono-substituted on carbon with halo, $(C_1-C_4)$alkyl, $(C_1-C_4)$alkoxy, hydroxy, amino, or mono-N— and di-N,N $(C_1-C_5)$ alkylamino provided that no quaternized nitrogen is included and there are no nitrogen-oxygen, nitrogen-nitrogen or nitrogen-halo bonds;

$R_{12}$ is piperazin-1-yl, 4-$(C_1-C_4)$alkylpiperazin-1-yl, 4-formylpiperazin-1-yl, morpholino, thiomorpholino, 1-oxothiomorpholino, 1,1-dioxo-thiomorpholino, thiazolidin-3-yl, 1-oxo-thiazolidin-3-yl, 1,1-dioxo-thiazolidin-3-yl, 2-$(C_1-C_6)$alkoxycarbonylpyrrolidin-1-yl, oxazolidin-3-yl or 2(R)-hydroxymethylpyrrolidin-1-yl; or $R_{12}$ is 3- and/or 4-mono-or di-substituted oxazetidin-2-yl, 2-, 4-, and/or 5-mono- or di-substituted oxazolidin-3-yl, 2-, 4-, and/or 5-mono- or di-substituted thiazolidin-3-yl, 2-, 4-, and/or 5-mono- or di- substituted 1-oxothiazolidin-3-yl, 2-, 4-, and/or 5-mono- or di-substituted 1,1-dioxothiazolidin-3-yl, 3- and/or 4-, mono- or di-substituted pyrrolidin-1-yl, 3-, 4- and/or 5-, mono-, di- or tri-substituted piperidin-1-yl, 3-, 4-, and/or 5-mono-, di-, or tri-substituted piperazin-1-yl, 3-substituted azetidin-1-yl, 4- and/or 5-, mono- or di-substituted 1,2-oxazinan-2-yl, 3-and/or 4-mono- or di-substituted pyrazolidin-1-yl, 4- and/or 5-, mono- or di-substituted isoxazolidin-2-yl, 4- and/or 5-, mono- and/or di-substituted isothiazolidin-2-yl wherein said $R_{12}$ substituents are independently H, halo, $(C_1-C_5)$-alkyl, hydroxy, amino, mono-N— or di-N,N—$(C_1-C_5)$ alkylamino, formyl, oxo, hydroxyimino, $(C_1-C_5)$ alkoxy, carboxy, carbamoyl, mono-N— or di-N,N— $(C_1-C_4)$alkylcarbamoyl, $(C_1-C_4)$alkoxyimino, $(C_1-C_4)$alkoxymethoxy, $(C_1-C_6)$alkoxycabonyl, carboxy$(C_1-C_5)$alkyl or hydroxy$(C_1-C_5)$alkyl;

with the proviso that if $R_4$ is H, methyl, ethyl or n-propyl $R_5$ is OH;

with the proviso that if $R_5$ and $R_7$ are H, then $R_4$ is not H, methyl, ethyl, n-propyl, hydroxy$(C_1-C_3)$alkyl or $(C_1-C_3)$alkoxy$(C_1-C_3)$alkyl and $R_6$ is $C(O)NR_8R_9$, $C(O)R_{12}$ or $(C_1-C_4)$alkoxycarbonyl.

A first group of preferred compounds of Formula I consists of those compounds wherein $R_1$ is 5-H, 5-halo, 5-methyl or 5-cyano;

$R_{10}$ and $R_{11}$ are each independently H or halo;

A is —C(H)=;

$R_2$ and $R_3$ are H;

$R_4$ is phenyl$(C_1-C_2)$alkyl wherein said phenyl groups are mono-, di- or tri-substituted independently with H or halo or mono- or di-substituted independently with H, halo, $(C_1-C_4)$alkyl, $(C_1-C_4)$alkoxy, trifluoromethyl, hydroxy, amino or cyano; or $R_4$ is thien-2- or -3-yl$(C_1-C_2)$alkyl, pyrid-2-, -3- or -4-yl $(C_1-C_2)$alkyl, thiazol-2-, -4- or -5-yl$(C_1-C_2)$alkyl, imidazol -1-, -2-, -4- or -5-yl$(C_1-C_2)$alkyl, fur-2- or -3-yl $(C_1-C_2)$alkyl, pyrrol-2- or -3-yl$(C_1-C_2)$alkyl, oxazol-2-, -4- or -5-yl-$(C_1-C_2)$alkyl, pyrazol-3, -4- or -5-yl $(C_1-C_2)$alkyl, isoxazol-3-, -4- or -5-yl$(C_1-C_2)$alkyl wherein said preceding $R_4$ heterocycles are optionally mono- or di-substituted independently with halo, trifluoromethyl, $(C_1-C_4)$alkyl, $(C_1-C_4)$alkoxy, amino or hydroxy and said mono- or di-substituents are bonded to carbon;

$R_5$ is hydroxy;

$R_6$ is $C(O)NR_8R_9$ or $C(O)R_{12}$; and $R_7$ is H.

Within the above first group of preferred compounds of Formula I is a first group of especially preferred compounds wherein the carbon atom a has (S) stereochemistry;

the carbon atom b has (R) stereochemistry;

$R_4$ is phenyl$(C_1-C_2)$alkyl, thien-2-yl-$(C_1-C_2)$alkyl, thien-3-yl-$(C_1-C_2)$alkyl, fur-2-yl-$(C_1-C_2)$alkyl or fur-3-yl-$(C_1-C_2)$alkyl wherein said rings are mono- or di-substituted independently with H or fluoro;

$R_6$ is $C(O)NR_8R_9$;

$R_8$ is $(C_1-C_3)$alkyl, hydroxy or $(C_1-C_3)$alkoxy; and $R_9$ is H, $(C_1-C_8)$alkyl, hydroxy, hydroxy$(C_1-C_6)$alkyl, $(C_1-C_8)$alkoxy, pyridyl, morpholinyl, piperazinyl, pyrrolidinyl, piperidinyl, imidazolyl or thiazolyl or $(C_1-C_4)$alkyl mono-substituted with pyridyl, morpholinyl, piperazinyl, pyrrolidinyl, piperidinyl, imidazolyl or thiazolyl.

Within the above first group of especially preferred compounds are the particularly preferred compounds 5-chloro-1H-indole-2-carboxylic acid [(1S)-((R)-hydroxy-dimethylcarbamoyl-methyl)-2-phenyl-ethyl]-amide, 5,6-dichloro-1H-indole-2-carboxylic acid {(1S)-[(R)-hydroxy-(methoxy-methyl-carbamoyl)-methyl]-2-phenyl-ethyl}-amide, 5-chloro-1H-indole-2-carboxylic acid {(1S)-[(R)-hydroxy-(methoxy-methyl-carbamoyl)-methyl]-2-phenyl-ethyl}-amide, 5-chloro-1H-indole-2-carboxylic acid ((1S)-{(R)-hydroxy-[(2-hydroxy-ethyl)-methyl-carbamoyl]-methyl}-2-phenyl-ethyl)-amide, 5-chloro-1H-indole-2-carboxylic acid [(1S)-benzyl-3-((3R,4S)-dihydroxy-pyrrolidin-1-yl)-(2R)-hydroxy-3-oxo-propyl]-amide, 5-chloro-1H-indole-2-carboxylic acid {(1S)-[(R)-hydroxy-(methyl-pyridin-2-yl-carbamoyl)-methyl]-2-phenyl-ethyl}-amide, and 5-chloro-1H-indole-2-carboxylic acid ((1S)-{(R)-hydroxy-[methyl-(2-pyridin-2-yl-ethyl)-carbamoyl]-methyl}-2-phenyl-ethyl)-amide.

Within the above first group of especially preferred compounds are the compounds wherein a. $R_1$ is 5-chloro;
$R_{10}$ and $R_{11}$ are H;
$R_4$ is benzyl;
$R_8$ is methyl; and
$R_9$ is methyl;

b. $R_1$ is 5-chloro;
$R_{11}$ is H;
$R_{10}$ is 6-chloro;
$R_4$ is benzyl;
$R_8$ is methyl; and
$R_9$ is methoxy;

c. $R_1$ is 5-chloro;
$R_{10}$ and $R_{11}$ are H;
$R_4$ is benzyl;
$R_8$ is methyl; and
$R_9$ methoxy;

d. $R_1$ is 5-chloro;
$R_{10}$ and $R_{11}$ are H;
$R_4$ is benzyl;
$R_8$ is methyl; and
$R_9$ is 2-(hydroxy)ethyl;

e. $R_1$ is 5-chloro;
$R_{10}$ and $R_{11}$ are H;
$R_4$ is benzyl;
$R_8$ is methyl; and
$R_9$ is pyridin-2-yl; and f. $R_1$ is 5-chloro;
$R_{10}$ and $R_{11}$ are H;
$R_4$ is benzyl;
$R_8$ is methyl; and
$R_9$ is 2-(pyridin-2-yl)ethyl.

Within the above first group of preferred compounds of Formula I is a second group of especially preferred compounds wherein the carbon atom a is (S) stereochemistry;
the carbon atom b is (R) stereochemistry;
$R_4$ is phenyl($C_1$–$C_2$)alkyl, thien-2-yl-($C_1$–$C_2$)alkyl, thien-3-yl-($C_1$–$C_2$)alkyl, fur-2-yl-($C_1$–$C_2$)alkyl or fur-3-yl-($C_1$–$C_2$)alkyl wherein said rings are mono- or di-substituted independently with H or fluoro;
$R_6$ is C(O)$R_{12}$; and
$R_{12}$ is morpholino, 4-($C_1$–$C_4$)alkylpiperazin-1-yl, 3-substituted azetidin-1-yl, 3- and/or 4-, mono- or di-substituted pyrrolidin-1-yl, 4- and/or 5- mono- or di-substituted isoxazolidin-2-yl, 4- and/or 5-, mono- or di-substituted 1,2-oxazinan-2-yl wherein said substituents are each independently H, halo, hydroxy, amino, mono-N— or di-N,N—($C_1$–$C_6$)alkylamino, oxo, hydroxyimino or alkoxy.

Within the above second group of especially preferred compounds are the particularly preferred compounds 5-chloro-1H-indole-2-carboxylic acid [(1S)-benzyl-(2R)-hydroxy-3-(4-methyl-piperazin-1-yl)-3-oxo-propyl]-amide hydrochloride, 5-chloro-1H-indole-2-carboxylic acid [(1S)-benzyl-(2R)-hydroxy-3-(3-hydroxy-azetidin-1-yl)-3-oxo-propyl]-amide, 5-chloro-1H-indole-2-carboxylic acid ((1S)-benzyl-(2R)-hydroxy-3-isoxazolidin-2-yl-3-oxo-propyl)-amide, 5-chloro-1H-indole-2-carboxylic acid ((1S)-benzyl-(2R)-hydroxy-3-[1,2]oxazinan-2-yl-3-oxo-propyl)-amide, 5-chloro-1H-indole-2-carboxylic acid [(1S)-benzyl-(2R)-hydroxy-3-((3S)-hydroxy-pyrrolidin-1-yl)-3-oxo-propyl]-amide, 5-chloro-1H-indole-2-carboxylic acid [(1S)-benzyl-3-((3S,4S)-dihydroxy-pyrrolidin-1-yl)-(2R)-hydroxy-3-oxo-propyl]-amide, 5-chloro-1H-indole-2-carboxylic acid [(1S)-benzyl-3-(cis-3,4-dihydroxy-pyrrolidin-1-yl)-(2R)-hydroxy-3-oxo-propyl]-amide, and 5-chloro-1H-indole-2-carboxylic acid ((1S)-benzyl-(2R)-hydroxy-3-morpholin-4-yl-3-oxo-propyl)-amide.

Within the above second group of especially preferred compounds are the compounds wherein a. $R_1$ is 5-chloro;
$R_{10}$ and $R_{11}$ are H;
$R_4$ is benzyl; and
$R_{12}$ is 4-methylpiperazin-1-yl;

b. $R_1$ is 5-chloro;
$R_{10}$ and $R_{11}$ are H;
$R_4$ is benzyl; and
$R_{12}$ is 3-hydroxyazetidin-1-yl;

c. $R_1$ is 5-chloro;
$R_{10}$ and $R_{11}$ are H;
$R_4$ is benzyl; and
$R_{12}$ is isoxazolidin-2-yl;

d. $R_1$ is 5-chloro;
$R_{10}$ and $R_{11}$ are H;
$R_4$ is benzyl; and
$R_{12}$ is (1,2)-oxazinan-2-yl;

e. $R_1$ is 5-chloro;
$R_{10}$ and $R_{11}$ are H;
$R_4$ is benzyl; and
$R_{12}$ is 3(S)-hydroxypyrrolidin-1-yl;

f. $R_1$ is 5-chloro;
$R_{10}$ and $R_{11}$ are H;
$R_4$ is benzyl; and
$R_{12}$ is (3S,4S)-dihydroxypyrrolidin-1-yl;

g. $R_1$ is 5-chloro;
$R_{10}$ and $R_{11}$ are H;
$R_4$ is benzyl; and
$R_{12}$ is cis-3,4-dihydroxypyrrolidin-1-yl; and h. $R_1$ is 5-chloro;
$R_{10}$ and $R_{11}$ are H;
$R_4$ is benzyl; and
$R_{12}$ is morpholino.

A second group of preferred compounds of Formula I consists of those compounds wherein $R_1$ is H, halo, methyl or cyano;
$R_{10}$ and $R_{11}$ are each independently H or halo;
A is —C(H)=;
$R_2$ and $R_3$ are H;
$R_4$ is phenyl($C_1$–$C_2$)alkyl wherein said phenyl groups are mono-, di- or tri-substituted independently with H or halo or mono- or di-substituted independently with H, halo, ($C_1$–$C_4$)alkyl, ($C_1$–$C_4$)alkoxy, trifluoromethyl, hydroxy, amino or cyano; or
$R_4$ is thien-2- or -3-yl($C_1$–$C_2$)alkyl, pyrid-2-, -3- or -4-yl ($C_1$–$C_2$)alkyl, thiazol-2-, -4- or -5-yl($C_1$–$C_2$)alkyl, imidazol -1-, -2-, -4- or -5-yl($C_1$–$C_2$)alkyl, fur-2- or -3-yl ($C_1$–$C_2$)alkyl, pyrrol-2- or -3-yl($C_1$–$C_2$)alkyl, oxazol-2-, -4- or -5-yl-($C_1$–$C_2$)alkyl, pyrazol-3-, -4- or -5-yl ($C_1$–$C_2$)alkyl, isoxazol-3-, -4- or -5-yl($C_1$–$C_2$)alkyl wherein said preceding $R_4$ heterocycles are optionally mono- or di-substituted independently with halo, trifluoromethyl, ($C_1$–$C_4$)alkyl, ($C_1$–$C_4$)alkoxy, amino or hydroxy and said mono- or di-substituents are bonded to carbon;

$R_5$ is hydroxy;

$R_6$ is carboxy or $(C_1-C_8)$alkoxycarbonyl; and $R_7$ is H, fluoro or $(C_1-C_6)$alkyl.

Within the second group of preferred compounds of Formula I is a group of especially preferred compounds wherein the carbon atom a is (S) stereochemistry;

the carbon atom b is (R) stereochemistry;

$R_4$ is phenyl$(C_1-C_2)$alkyl, thien-2-yl-$(C_1-C_2)$alkyl, thien-3-yl-$(C_1-C_2)$alkyl, fur-2-yl-$(C_1-C_2)$alkyl, or fur-3-yl-$(C_1-C_2)$alkyl wherein said rings are mono- or di-substituted independently with H or fluoro;

$R_{10}$ and $R_{11}$ are H;

$R_6$ is carboxy; and $R_7$ is H.

Preferred within the immediately preceding group is a compound wherein $R_1$ is 5-chloro;

$R_{10}$ and $R_{11}$ are H; and $R_4$ is benzyl.

A third group of preferred compounds of Formula I consists of those compounds wherein $R_1$ is H, halo, methyl or cyano;

$R_{10}$ and $R_{11}$ are each independently H or halo;

A is —C(H)=;

$R_2$ and $R_3$ are H;

$R_4$ is phenyl$(C_1-C_2)$alkyl wherein said phenyl groups are mono-, di- or tri-substituted independently with H or halo or mono- or di-substituted independently with H, halo, $(C_1-C_4)$alkyl, $(C_1-C_4)$alkoxy, trifluoromethyl, hydroxy, amino or cyano; or $R_4$ is thien-2- or -3-yl$(C_1-C_2)$alkyl, pyrid-2-, -3- or -4-yl $(C_1-C_2)$alkyl, thiazol-2-, -4- or -5-yl$(C_1-C_2)$alkyl, imidazol -1-, -2-, -4- or -5-yl$(C_1-C_2)$alkyl, fur-2- or -3-yl $(C_1-C_2)$alkyl, pyrrol-2- or -3-yl$(C_1-C_2)$alkyl, oxazol-2-, -4- or -5-yl-$(C_1-C_2)$alkyl, pyrazol-3-, -4- or -5-yl $(C_1-C_2)$alkyl, isoxazol-3-, -4- or -5-yl$(C_1-C_2)$alkyl wherein said preceding $R_4$ heterocycles are optionally mono- or di-substituted independently with halo, trifluoromethyl, $(C_1-C_4)$alkyl, $(C_1-C_4)$alkoxy, amino or hydroxy and said mono- or di-substituents are bonded to carbon;

$R_5$ is fluoro, $(C_1-C_4)$alkyl, $(C_1-C_5)$alkoxy, amino$(C_1-C_4)$alkoxy, mono-N— or di-N,N—$(C_1-C_2)$alkylamino $(C_1-C_4)$alkoxy, carboxy$(C_1-C_4)$alkoxy, $(C_1-C_5)$alkoxy-carbonyl$(C_1-C_4)$alkoxy, benzyloxycarbonyl $(C_1-C_4)$alkoxy;

$R_6$ is carboxy or $(C_1-C_8)$alkoxycarbonyl; and $R_7$ is H, fluoro or $(C_1-C_6)$alkyl.

A fourth group of preferred compounds of Formula I consists of those compounds wherein $R_1$ is H, halo, methyl or cyano;

$R_{10}$ and $R_{11}$ are each independently H or halo;

A is —C(H)=;

$R_2$ and $R_3$ are H;

$R_4$ is phenyl$(C_1-C_2)$alkyl wherein said phenyl groups are mono-, di- or tri-substituted independently with H or halo or mono- or di-substituted independently with H, halo, $(C_1-C_4)$alkyl, $(C_1-C_4)$alkoxy, trifluoromethyl, hydroxy, amino or cyano; or $R_4$ is thien-2- or -3-yl$(C_1-C_2)$alkyl, pyrid-2-, -3- or -4-yl $(C_1-C_2)$alkyl, thiazol-2-, -4- or -5-yl$(C_1-C_2)$alkyl, imidazol -1-, -2-, -4- or -5-yl$(C_1-C_2)$alkyl, fur-2- or -3-yl $(C_1-C_2)$alkyl,pyrrol-2- or -3-yl$(C_1-C_2)$alkyl, oxazol-2-, -4- or -5-yl-$(C_1-C_2)$alkyl, pyrazol-3-, -4- or -5-yl $(C_1-C_2)$alkyl, isoxazol-3-, -4- or -5-yl$(C_1-C_2)$alkyl wherein said preceding $R_4$ heterocycles are optionally mono- or di-substituted independently with halo, trifluoromethyl, $(C_1-C_4)$alkyl, $(C_1-C_4)$alkoxy, amino or hydroxy and said mono- or di-substituents are bonded to carbon;

$R_5$ is fluoro, $(C_1-C_4)$alkyl, $(C_1-C_5)$alkoxy, amino$(C_1-C_4)$alkoxy, mono-N— or di-N,N—$(C_1-C_4)$alkylamino $(C_1-C_4)$alkoxy, carboxy$(C_1-C_4)$alkoxy, $(C_1-C_5)$alkoxy-carbonyl$(C_1-C_4)$alkoxy, benzyloxycarbonyl $(C_1-C_4)$alkoxy;

$R_6$ is C(O)NR$_8$R$_9$ or C(O)R$_{12}$; and $R_7$ is H, fluoro or $(C_1-C_6)$alkyl.

Another group of glycogen phosphorylase inhibitors includes compounds of the Formula IA

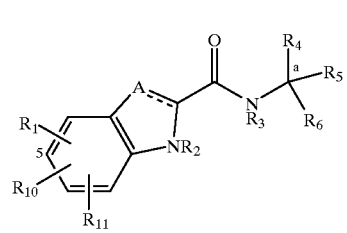

Formula IA and the pharmaceutically acceptable salts and prodrugs thereof wherein the dotted line (—) is an optional bond;

A is —C(H)=, —C((C$_1$–C$_4$)alkyl)=, —C(halo)= or —N=, when the dotted line (—) is a bond, or A is methylene or —CH((C$_1$–C$_4$)alkyl)-, when the dotted line (—) is not a bond;

$R_1$, $R_{10}$ or $R_{11}$ are each independently H, halo, cyano, 4-, 6-, or 7-nitro, $(C_1-C_4)$alkyl, $(C_1-C_4)$alkoxy, fluoromethyl, difluoromethyl or trifluoromethyl;

$R_2$ is H;

$R_3$ is H or $(C_1-C_5)$alkyl;

$R_4$ is H, methyl, ethyl, n-propyl, hydroxy$(C_1-C_3)$alkyl, $(C_1-C_3)$alkoxy$(C_1-C_3)$alkyl, phenyl$(C_1-C_4)$alkyl, phenylhydroxy$(C_1-C_4)$alkyl, (phenyl)((C$_1$–C$_4$)-alkoxy)$(C_1-C_4)$alkyl, thien-2- or -3-yl$(C_1-C_4)$alkyl or fur-2- or -3-yl$(C_1-C_4)$alkyl wherein said $R_4$ rings are mono-, di- or tri-substituted independently on carbon with H, halo, $(C_1-C_4)$alkyl, $(C_1-C_4)$alkoxy, trifluoromethyl, hydroxy, amino, cyano or 4,5-dihydro-1H-imidazol-2-yl; or $R_4$ is pyrid-2-, -3- or -4-yl$(C_1-C_4)$alkyl, thiazol-2-, -4- or -5-yl$(C_1-C_4)$alkyl, imidazol-2-, -4- or -5-yl$(C_1-C_4)$ alkyl, pyrrol-2- or -3-yl$(C_1-C_4)$alkyl, oxazol-2-, -4- or -5-yl$(C_1-C_4)$alkyl, pyrazol-3-, -4- or -5-yl$(C_1-C_4)$ alkyl, isoxazol-3-, -4- or -5-yl$(C_1-C_4)$alkyl, isothiazol-3-, -4- or -5-yl$(C_1-C_4)$alkyl, pyridazin-3- or -4-yl $(C_1-C_4)$alkyl, pyrimidin-2-, -4-, -5- or -6-yl$(C_1-C_4)$ alkyl, pyrazin-2- or -3-yl$(C_1-C_4)$alkyl, 1,3,5-triazin-2-yl$(C_1-C_4)$alkyl or indol-2-$(C_1-C_4)$alkyl, wherein said preceding $R_4$ heterocycles are optionally mono- or di-substituted independently with halo, trifluoromethyl, $(C_1-C_4)$alkyl, $(C_1-C_4)$alkoxy, amino, hydroxy or cyano and said substituents are bonded to carbon; or $R_4$ is $R_{15}$-carbonyloxymethyl, wherein said $R_{15}$ is phenyl, thiazolyl, imidazolyl, 1H-indolyl, furyl, pyrrolyl, oxazolyl, pyrazolyl, isoxazolyl, isothiazolyl, pyridyl, pyridazinyl, pyrimidinyl, pyrazinyl or 1,3,5-triazinyl and wherein said preceding $R_{15}$ rings are optionally mono- or di-substituted independently with halo, amino, hydroxy, $(C_1-C_4)$alkyl, $(C_1-C_4)$alkoxy or trifluoromethyl and said mono- or di-substituents are bonded to carbon;

$R_5$ is H;

$R_6$ is carboxy, $(C_1-C_8)$alkoxycarbonyl, benzyloxycarbonyl, $C(O)NR_8R_9$ or $C(O)R_{12}$ wherein $R_8$ is H, $(C_1-C_6)$alkyl, cyclo$(C_3-C_6)$alkyl, cyclo$(C_3-C_6)$alkyl$(C_1-C_5)$alkyl, hydroxy or $(C_1-C_8)$alkoxy; and $R_9$ is H, cyclo$(C_3-C_8)$alkyl, cyclo$(C_3-C_8)$alkyl$(C_1-C_5)$alkyl, cyclo$(C_4-C_7)$alkenyl, cyclo$(C_3-C_7)$alkyl$(C_1-C_5)$alkoxy, cyclo$(C_3-C_7)$alkyloxy, hydroxy, methylene-perfluorinated$(C_1-C_8)$alkyl, phenyl, or a heterocycle wherein said heterocycle is pyridyl, furyl, pyrrolyl, pyrrolidinyl, oxazolyl, thiazolyl, imidazolyl, pyrazolyl, pyrazolinyl, pyrazolidinyl, isoxazolyl, isothiazolyl, pyranyl, pyridinyl, piperidinyl, morpholinyl, pyridazinyl, pyrimidinyl, pyrazinyl, piperazinyl, 1,3,5-triazinyl, benzothiazolyl, benzoxazolyl, benzimidazolyl, thiochromanyl or tetrahydrobenzothiazolyl wherein said heterocycle rings are carbon-nitrogen linked; or $R_9$ is $(C_1-C_6)$alkyl or $(C_1-C_8)$alkoxy wherein said $(C_1-C_6)$alkyl or $(C_1-C_8)$alkoxy is optionally monosubstituted with cyclo$(C_4-C_7)$alken-1-yl, phenyl, thienyl, pyridyl, furyl, pyrrolyl, pyrrolidinyl, oxazolyl, thiazolyl, imidazolyl, pyrazolyl, pyrazolinyl, pyrazolidinyl, isoxazolyl, isothiazolyl, pyranyl, piperidinyl, morpholinyl, thiomorpholinyl, 1-oxothiomorpholinyl, 1,1-dioxothiomorpholinyl, pyridazinyl, pyrimidinyl, pyrazinyl, piperazinyl, 1,3,5-triazinyl or indolyl and wherein said $(C_1-C_6)$alkyl or $(C_1-C_8)$alkoxy are optionally additionally independently mono- or di-substituted with halo, hydroxy, $(C_1-C_5)$alkoxy, amino, mono-N— or di-N,N—$(C_1-C_5)$alkylamino, cyano, carboxy, or $(C_1-C_4)$alkoxycarbonyl; and wherein the $R_9$ rings are optionally mono- or di-substituted independently on carbon with halo, $(C_1-C_4)$alkyl, $(C_1-C_4)$alkoxy, hydroxy, hydroxy$(C_1-C_4)$alkyl, amino$(C_1-C_4)$alkyl, mono-N— or di-N, N—$(C_1-C_4)$alkylamino$(C_1-C_4)$alkyl, $(C_1-C_4)$alkoxy$(C_1-C_4)$alkyl, amino, mono-N— or di-N,N—$(C_1-C_4)$alkylamino, cyano, carboxy, $(C_1-C_5)$alkoxycarbonyl, carbamoyl, formyl or trifluoromethyl and said $R_9$ rings may optionally be additionally mono- or di-substituted independently with $(C_1-C_5)$alkyl or halo;

with the proviso that no quaternized nitrogen on any $R_9$ heterocycle is included;

$R_{12}$ is morpholino, thiomorpholino, 1-oxothiomorpholino, 1,1-dioxothiomorpholino, thiazolidin-3-yl, 1-oxothiazolidin-3-yl, 1,1-dioxothiazolidin-3-yl, pyrrolidin-1-yl, piperidin-1-yl, piperazin-1-yl, piperazin-4-yl, azetidin-1-yl, 1,2-oxazinan-2-yl, pyrazolidin-1-yl, isoxazolidin-2-yl, isothiazolidin-2-yl, 1,2-oxazetidin-2-yl, oxazolidin-3-yl, 3,4-dihydroisoquinolin-2-yl, 1,3-dihydroisoindol-2-yl, 3,4-dihydro-2H-quinol-1-yl, 2,3-dihydro-benzo[1,4]oxazin-4-yl, 2,3-dihydro-benzo[1,4]-thiazine-4-yl, 3,4-dihydro-2H-quinoxalin-1-yl, 3,4-dihydro-benzo[c][1,2]oxazin-1-yl, 1,4-dihydro-benzo[d]3,4-dihydro-benzo[e][1,2]-oxazin-2-yl, 3H-benzo[d]isoxazol-2-yl, 3H-benzo[c]isoxazol-1-yl or azepan-1-yl, wherein said $R_{12}$ rings are optionally mono-, di- or tri-substituted independently with halo, $(C_1-C_5)$alkyl, $(C_1-C_5)$alkoxy, hydroxy, amino, mono-N— or di-N, N—$(C_1-C_5)$alkylamino, formyl, carboxy, carbamoyl, mono-N— or di-N,N—$(C_1-C_5)$alkylcarbamoyl, $(C_1-C_6)$alkoxy$(C_1-C_3)$alkoxy, $(C_1-C_5)$alkoxycarbonyl, benzyloxycarbonyl, $(C_1-C_5)$alkoxycarbonyl$(C_1-C_5)$alkyl, $(C_1-C_4)$alkoxycarbonylamino, carboxy$(C_1-C_5)$alkyl, carbamoyl$(C_1-C_5)$alkyl, mono-N— or di-N,N—$(C_1-C_5)$alkylcarbamoyl$(C_1-C_5)$alkylcarbamoyl$(C_1-C_5)$alkyl, hydroxy$(C_1-C_5)$alkyl, $(C_1-C_4)$alkoxy$(C_1-C_4)$alkyl, amino$(C_1-C_4)$alkyl, mono-N— or di-N, N—$(C_1-C_4)$alkylamino$(C_1-C_4)$alkyl, oxo, hydroxyimino or $(C_1-C_6)$alkoxyimino and wherein no more than two substituents are selected from oxo, hydroxyimino or $(C_1-C_6)$alkoxyimino and oxo, hydroxyimino or $(C_1-C_6)$alkoxyimino are on nonaromatic carbon; and wherein said $R_{12}$ rings are optionally additionally mono- or di-substituted independently with $(C_1-C_5)$alkyl or halo;

with the proviso that when $R_6$ is $(C_1-C_5)$alkoxycarbonyl or benzyloxycarbonyl then $R_1$ is 5-halo, 5-$(C_1-C_4)$alkyl or 5-cyano and $R_4$ is (phenyl)(hydroxy)$(C_1-C_4)$alkyl, (phenyl)($(C_1-C_4)$alkoxy)$(C_1-C_4)$alkyl, hydroxymethyl or Ar$(C_1-C_2)$alkyl, wherein Ar is thien-2- or -3-yl, fur-2- or -3-yl or phenyl wherein said Ar is optionally mono- or di-substituted independently with halo; with the proviso that when $R_1$ and $R_{10}$ and $R_{11}$ are H, $R_4$ is not imidazol-4-ylmethyl, 2-phenylethyl or 2-hydroxy-2-phenylethyl;

with the proviso that when $R_8$ is H and $R_9$ is $(C_1-C_6)$alkyl, $R_9$ is not substituted with carboxy or $(C_1-C_4)$alkoxycarbonyl on the carbon which is attached to the nitrogen atom N of NHR$_9$;

with the proviso that when $R_6$ is carboxy and $R_1, R_{10}, R_{11}$ and $R_5$ are all H, then $R_4$ is not benzyl, H, (phenyl)(hydroxy)methyl, methyl, ethyl or n-propyl; and with the proviso that when $R_8$ and $R_9$ are both n-pentyl, $R^1$ is 5-chloro, 5-bromo, 5-cyano, 5-$(C_1-C_5$ alkyl), 5-$(C_1-C_5$alkoxy), or 5-trifluoromethyl.

A first group of preferred compounds of Formula IA consists of those compounds wherein $R_1$ is 5-H, 5-halo, 5-methyl, 5-cyano or 5-trifluoromethyl;

$R_{10}$ and $R_{11}$ are each independently H or halo;

A is —C(H)=;

$R_2$ and $R_3$ are H;

$R_4$ is H, methyl, phenyl$(C_1-C_2)$alkyl, wherein said phenyl groups are mono- or di-substituted independently with H, halo, $(C_1-C_4)$alkyl, $(C_1-C_4)$alkoxy, trifluoromethyl, hydroxy, amino or cyano and wherein said $R_4$ groups are optionally additionally mono-substituted with halo; or $R_4$ is thien-2- or -3-yl$(C_1-C_2)$alkyl, pyrid-2-, -3- or -4-yl $(C_1-C_2)$alkyl, thiazol-2-, -4- or -5-yl$(C_1-C_2)$alkyl, imidazol-2-, -4- or -5-yl$(C_1-C_2)$alkyl, fur-2- or -3-yl $(C_1-C_2)$alkyl, pyrrol-2- or -3-yl$(C_1-C_2)$alkyl, oxazol-2-, -4- or -5-yl$(C_1-C_2)$alkyl, pyrazol-3-, -4- or -5-yl $(C_1-C_2)$alkyl, isoxazol-3-, -4- or -5-yl$(C_1-C_2)$alkyl, isothiazol-3-, -4- or -5-yl$(C_1-C_2)$alkyl, pyridazin-3- or -4-yl$(C_1-C_2)$alkyl, pyrimidin-2-, -4-, -5- or -6-yl $(C_1-C_2)$alkyl, pyrazin-2- or -3-yl$(C_1-C_2)$alkyl or 1,3,5-triazin-2-yl$(C_1-C_2)$alkyl wherein said preceding $R_4$ heterocycles are optionally mono- or di-substituted independently with halo, trifluoromethyl, $(C_1-C_4)$ alkyl, $(C_1-C_4)$alkoxy, amino or hydroxy and said mono- or di-substituents are bonded to carbon;

$R_5$ is H; and $R_6$ is $C(O)NR_8R_9$ or $C(O)R_{12}$.

Within the above first group of preferred compounds of Formula IA is a first group of especially preferred compounds wherein $R_4$ is H, phenyl$(C_1-C_2)$alkyl, thien-2- or -3-yl$(C_1-C_2)$ alkyl, fur-2- or -3-yl$(C_1-C_2)$alkyl wherein said $R_4$ rings are mono- or di-substituted independently with H or fluoro;

$R_6$ is $C(O)R_{12}$; and $R_{12}$ is morpholino, thiomorpholino, 1-oxothiomorpholino, 1,1-dioxothiomorpholino, thiazolidin-3-yl, 1-oxothiazolidin-3-yl, 1,1-dioxothiazolidin-3-yl, pyrrolidin-1-yl, piperidin-1-yl, piperazin-1-yl, piperazin-4-yl, azetidin-1-yl, 1,2-oxazinan-2-yl, isoxazolidin-2-yl, isothiazolidin-2-yl, 1,2-oxazetidin-2-yl, oxazolidin-3-yl, 1,3-dihydroisoindol-2-yl, or azepan-1-yl, wherein said $R_{12}$ rings are optionally mono- or di-substituted independently with halo, $(C_1-C_5)$alkyl, $(C_1-C_5)$alkoxy, hydroxy, amino, mono-N— or di-N, N—$(C_1-C_5)$alkylamino, formyl, carboxy, carbamoyl, mono-N— or di-N,N—$(C_1-C_5)$alkylcarbamoyl, $(C_1-C_5)$alkoxycarbonyl, hydroxy$(C_1-C_5)$alkyl, amino $(C_1-C_4)$alkyl, mono-N— or di-N,N—$(C_1-C_4)$ alkylamino$(C_1-C_4)$alkyl, oxo, hydroxyimino or $(C_1-C_6)$alkoxyimino with the proviso that only the $R_{12}$ heterocycles thiazolidin-3-yl, pyrrolidin-1-yl, piperidin-1-yl, piperazin-1-yl, piperazin-4-yl, azetidin-1-yl, 1,2-oxazinan-2-yl, isoxazolidin-2-yl, or oxazolidin-3-yl are optionally mono- or di-substituted with oxo, hydroxyimino, or $(C_1-C_6)$alkoxyimino; and wherein said $R_{12}$ rings are optionally additionally mono- or di-substituted independently with $(C_1-C_5)$alkyl.

Within the above group of especially preferred compounds are the compounds 5-chloro-1H-indole-2-carboxylic acid [(1S)-benzyl-2-(3-hydroxyimino-pyrrolidin-1-yl)-2-oxo-ethyl]-amide, 5-chloro-1H-indole-2-carboxylic acid [2-(cis-3,4-dihydroxy-pyrrolidin-1-yl)-2-oxo-ethyl]-amide, 5-chloro-1H-indole-2-carboxylic acid [2-((3S,4S)-dihydroxy-pyrrolidin-1-yl)-2-oxo-ethyl]-amide, 5-chloro-1H-indole-2-carboxylic acid [(1S)-benzyl-2-(cis-3,4-dihydroxy-pyrrolidin-1-yl)-2-oxo-ethyl]-amide, 5-chloro-1H-indole-2-carboxylic acid [2-(1,1-dioxo-thiazolidin-3-yl)-2-oxo-ethyl]-amide, 5-chloro-1H-indole-2-carboxylic acid (2-oxo-2-thiazolidin-3-yl-ethyl)-amide, 5-chloro-1H-indole-2-carboxylic acid [(1S)-(4-fluoro-benzyl)-2-(4-hydroxy-piperidin-1-yl)-oxo-ethyl]-amide, 5-chloro-1H-indole-2-carboxylic acid [(1S)-benzyl-2-((3RS)-hydroxy-piperidin-1-yl)-2-oxo-ethyl]-amide, 5-chloro-1H-indole-2-carboxylic acid [2-oxo-2-((1RS)-oxo-1-thiazolidin-3-yl)-ethyl]-amide, 5-chloro-1H-indole-2-carboxylic acid [(1S)-(2-fluoro-benzyl)-2-(4-hydroxy-piperidin-1-yl)-2-oxo-ethyl]-amide, 5-chloro-1H-indole-2-carboxylic acid [(1S)-benzyl-2-((3S,4S)-dihydroxy-pyrrolidin-1-yl)-2-oxo-ethyl]-amide, 5-chloro-1H-indole-2-carboxylic acid [(1S)-benzyl-2-(3-hydroxy-azetidin-1-yl)-2-oxo-ethyl]-amide, 5-chloro-1H-indole-2-carboxylic acid [(1S)-benzyl-2-(3-hydroxyimino-azetidin-1-yl)-2-oxo-ethyl]-amide, 5-chloro-1H-indole-2-carboxylic acid [(1S)-benzyl-2-(4-hydroxyimino-piperidin-1-yl)-2-oxo-ethyl]-amide, and 5-chloro-1H-indole-2-carboxylic acid [1-benzyl-2-(3-hydroxypyrrolidin-1-yl)-2-oxo-ethyl]amide.

Within the above group of especially preferred compounds is a first group of particularly preferred compounds wherein $R_4$ is H; and $R_{12}$ is thiazolidin-3-yl, 1-oxo-thiazolidin-3-yl, 1,1-dioxo-thiazolidin-3-yl or oxazolidin-3-yl or said $R_{12}$ substituents optionally mono- or di-substituted independently with carboxy, $(C_1-C_5)$alkoxycarbonyl, hydroxy $(C_1-C_3)$alkyl, amino$(C_1-C_3)$alkyl, mono-N— or di-N, N—$(C_1-C_3)$alkylamino$(C_1-C_3)$alkyl or $R_{12}$ is mono- or di-substituted pyrrolidin-1-yl wherein said substituents are independently carboxy, $(C_1-C_5)$ alkoxycarbonyl, $(C_1-C_5)$alkoxy, hydroxy, hydroxy $(C_1-C_3)$alkyl, amino, amino$(C_1-C_3)$alkyl, mono-N— or di-N,N—$(C_1-C_3)$alkylamino$(C_1-C_3)$alkyl or mono-N— or di-N,N—$(C_1-C_4)$alkylamino; and the $R_{12}$ rings are optionally additionally independently disubstituted with $(C_1-C_5)$alkyl.

Preferred compounds within the immediately preceding group of particularly preferred compounds are compounds wherein a. $R_1$ is 5-chloro;
$R_{10}$ and $R_{11}$ are H; and
$R_{12}$ is cis-3,4-dihydroxy-pyrrolidin-1-yl;

b. $R_1$ is 5-chloro;
$R_{10}$ and $R_{11}$ are H; and
$R_{12}$ is (3S,4S)-dihydroxy-pyrrolidin-1-yl;

c. $R_1$ is 5-chloro;
$R_{10}$ and $R_{11}$ are H; and
$R_{12}$ is 1,1-dioxo-thiazolidin-3-yl;

d. $R_1$ is 5-chloro;
$R_{10}$ and $R_{11}$ are H; and
$R_{12}$ is thiazolidin-3-yl; and e. $R_1$ is 5-chloro;
$R_{10}$ and $R_{11}$ are H; and
$R_{12}$ is 1-oxo-thiazolidin-3-yl.

Within the above group of especially preferred compounds is a second group of particularly preferred compounds wherein $R_4$ is phenylmethyl, thien-2- or -3-ylmethyl wherein said $R_4$ rings are optionally mono- or di-substituted with fluoro; and $R_{12}$ is thiazolidin-3-yl, 1-oxo-thiazolidin-3-yl, 1,1-dioxo-thiazolidin-3-yl or oxazolidin-3-yl or said $R_{12}$ substituents optionally mono- or di-substituted independently with carboxy or $(C_1-C_5)$alkoxycarbonyl, hydroxy $(C_1-C_3)$alkyl, amino$(C_1-C_3)$alkyl or mono-N— or di-N,N—$(C_1-C_3)$alkylamino$(C_1-C_3)$alkyl or $R_{12}$ is mono- or di-substituted azetidin-1-yl or mono- or di-substituted pyrrolidin-1-yl or mono- or di-substituted piperidin-1-yl wherein said substituents are independently carboxy, $(C_1-C_5)$alkoxycarbonyl, hydroxy$(C_1-C_3)$alkyl, amino$(C_1-C_3)$alkyl, mono-N— or di-N,N—$(C_1-C_3)$alkylamino$(C_1-C_3)$alkyl, hydroxy, $(C_1-C_5)$alkoxy, amino, mono-N— or di-N,N—$(C_1-C_5)$ alkylamino, oxo, hydroxyimino or $(C_1-C_5)$ alkoxyimino; and the $R_{12}$ rings are optionally additionally mono- or di-substituted independently with $(C_1–C_5)$alkyl.

Preferred compounds within the immediately preceding group of particularly preferred compounds are compounds wherein a. $R_1$ is 5-chloro;
   $R_{10}$ and $R_{11}$ are H;
   $R_4$ is 4-fluorobenzyl;
   $R_{12}$ is 4-hydroxypiperidin-1-yl; and the stereochemistry of carbon (a) is (S);

b. $R_1$ is 5-chloro;
   $R_{10}$ and $R_{11}$ are H;
   $R_4$ is benzyl;
   $R_{12}$ is 3-hydroxypiperidin-1-yl; and the stereochemistry of carbon (a) is (S);

c. $R_1$ is 5-chloro;
   $R_{10}$ and $R_{11}$ are H;
   $R_4$ is benzyl;
   $R_{12}$ is cis-3,4-dihydroxy-pyrrolidin-1-yl; and the stereochemistry of carbon (a) is S;

d. $R_1$ is 5-chloro;
   $R_{10}$ and $R_{11}$ are H; $R_4$ is benzyl;
   $R_{12}$ is 3-hydroxyimino-pyrrolidin-1-yl; and the stereochemistry of carbon (a) is (S);

e. $R_1$ is 5-chloro;
   $R_{10}$ and $R_{11}$ are H;
   $R_4$ is 2-fluorobenzyl;
   $R_{12}$ is 4-hydroxypiperidin-1-yl; and the stereochemistry of carbon (a) is (S);

f. $R_1$ is 5-chloro;
   $R_{10}$ and $R_{11}$ are H;
   $R_4$ is benzyl;
   $R_{12}$ is (3S,4S)-dihydroxy-pyrrolidin-1-yl; and the stereochemistry of carbon (a) is (S);

g. $R_1$ is 5-chloro;
   $R_{10}$ and $R_{11}$ are H;
   $R_4$ is benzyl;
   $R_{12}$ is 3-hydroxy-azetidin-1-yl; and the stereochemistry of carbon (a) is (S);

h. $R_1$ is 5-chloro;
   $R_{10}$ and $R_{11}$ are H;
   $R_4$ is benzyl;
   $R_{12}$ is 3-hydroxyimino-azetidin-1-yl; and the stereochemistry of carbon (a) is (S); and i. $R_1$ is 5-chloro;
   $R_{10}$ and $R_{11}$ are H;
   $R_4$ is benzyl;
   $R_{12}$ is 4-hydroxyimino-piperidin-1-yl; and the stereochemistry of carbon (a) is (S).

A second group of especially preferred compounds within the first group of preferred compounds are the compounds wherein $R_4$ is H, phenyl$(C_1–C_2)$alkyl, thien-2- or -3-yl$(C_1–C_2)$alkyl, fur-2- or -3-yl$(C_1–C_2)$alkyl wherein said $R_4$ rings are mono- or di-substituted independently with H or fluoro;

$R_6$ is $C(O)NR_8R_9$; and $R_8$ is H, $(C_1–C_5)$alkyl, hydroxy or $(C_1–C_4)$alkoxy; and $R_9$ is H, cyclo$(C_4–C_6)$alkyl, cyclo$(C_3–C_6)$alkyl$(C_1–C_5)$alkyl, methylene-perfluorinated$(C_1–C_3)$alkyl, pyridyl, pyrrolidinyl, oxazolyl, thiazolyl, imidazolyl, piperidinyl, benzothiazolyl or thiochromanyl; or $R_9$ is $(C_1–C_5)$alkyl wherein said $(C_1–C_5)$alkyl is optionally substituted with cyclo$(C_4–C_6)$alkenyl, phenyl, thienyl, pyridyl, pyrrolidinyl, oxazolyl, thiazolyl, imidazolyl, pyrazolyl, piperidinyl, morpholinyl, thiomorpholinyl, 1-oxothiomorpholinyl, or 1,1-dioxothiomorpholinyl and wherein said $(C_1–C_5)$alkyl or $(C_1–C_4)$alkoxy is optionally additionally independently mono- or di-substituted with halo, hydroxy, $(C_1–C_5)$alkoxy, amino, mono-N— or di-N,N—$(C_1–C_5)$alkylamino, cyano, carboxy, or $(C_1–C_4)$alkoxycarbonyl; and wherein the $R_9$ rings are optionally mono- or di-substituted independently on carbon with halo, $(C_1–C_4)$alkyl, $(C_1–C_4)$alkoxy, hydroxy, amino, mono-N— or di-N,N—$(C_1–C_4)$alkylamino, carbamoyl, $(C_1–C_5)$alkoxycarbonyl or carbamoyl.

Within the immediately preceding second group of especially preferred compounds are the compounds wherein a. $R_1$ is 5-chloro;
   $R_{10}$ and $R_{11}$ are H;
   $R_4$ is benzyl;
   $R_8$ is methyl; and
   $R_9$ is 3-(dimethylamino)propyl;

b. the stereochemistry of carbon (a) is (S);
   $R_1$ is 5-chloro;
   $R_{10}$ and $R_{11}$ are H;
   $R_4$ is benzyl;
   $R_8$ is methyl; and
   $R_9$ is 3-pyridyl;

c. the stereochemistry of carbon (a) is (S);
   $R_1$ is 5-chloro;
   $R_{10}$ and $R_{11}$ are H;
   $R_4$ is benzyl;
   $R_8$ is methyl; and
   $R_9$ is 2-hydroxyethyl; and d. the stereochemistry of carbon (a) is (S);
   $R_1$ is 5-fluoro;
   $R_{10}$ and $R_{11}$ are H;
   $R_4$ is 4-fluorophenylmethyl;
   $R_8$ is methyl; and
   $R_9$ is 2-morpholinoethyl.

A third group of especially preferred compounds within the first group of preferred compounds are the compounds wherein $R_4$ is H, phenyl$(C_1–C_2)$alkyl, thien-2- or -3-yl$(C_1–C_2)$alkyl, fur-2- or -3-yl$(C_1–C_2)$alkyl wherein said $R_4$ rings are mono- or di-substituted independently with H or fluoro;

$R_6$ is $C(O)NR_8R_9$; and $R_8$ is H, $(C_1–C_5)$alkyl, hydroxy or $(C_1–C_4)$alkoxy; and $R_9$ is $(C_1–C_4)$alkoxy wherein said $(C_1–C_4)$alkoxy is optionally substituted with cyclo$(C_4–C_6)$alkenyl, phenyl, thienyl, pyridyl, pyrrolidinyl, oxazolyl, thiazolyl, imidazolyl, pyrazolyl, piperidinyl, morpholinyl, thiomorpholinyl, 1-oxothiomorpholinyl, or 1,1-dioxothiomorpholinyl and wherein said $(C_1–C_5)$alkyl or $(C_1–C_4)$alkoxy is optionally additionally independently mono- or di-substituted with halo, hydroxy, $(C_1–C_5)$alkoxy, amino, mono-N— or di-N,N—$(C_1–C_5)$alkylamino, cyano, carboxy, or $(C_1–C_4)$alkoxycarbonyl; and wherein the $R_9$ rings are optionally mono- or di-substituted independently on carbon with halo, $(C_1–C_4)$alkyl, $(C_1–C_4)$alkoxy, hydroxy, amino, mono-N— or di-N,N—$(C_1–C_4)$alkylamino, carbamoyl, $(C_1–C_5)$alkoxycarbonyl or carbamoyl.

Within the immediately preceding third group of especially preferred compounds are the compounds wherein a. $R_1$ is 5-chloro;
   $R_{10}$ and $R_{11}$ are H;
   $R_4$ is benzyl;
   $R_8$ is methyl; and
   $R_8$ is 2-hydroxyethoxy;
b. the stereochemistry of carbon (a) is (S);
   $R_1$ is 5-chloro;
   $R_{10}$ and $R_{11}$ are H;
   $R_4$ is 4-fluorophenylmethyl;
   $R_8$ is methyl; and
   $R_9$ is methoxy;
c. the stereochemistry of carbon (a) is (S);
   $R_1$ is 5-chloro;
   $R_{10}$ and $R_{11}$ are H;
   $R_4$ is benzyl;
   $R_8$ is methyl; and
   $R_9$ is methoxy;

A second group of preferred compounds of Formula IA are those compounds wherein
   $R_1$ is 5-halo, 5-methyl, 5-cyano or trifluoromethyl;
   $R_{10}$ and $R_{11}$ are each independently H or halo;
   A is —C(H)=;
   $R_2$ and $R_3$ are H;
   $R_4$ is H, phenyl($C_1$–$C_2$)alkyl, thien-2- or -3-yl($C_1$–$C_2$) alkyl, fur-2- or -3-yl($C_1$–$C_2$)alkyl wherein said rings are mono- or di-substituted independently with H or fluoro;
   $R_5$ is H; and
   $R_6$ is ($C_1$–$C_5$)alkoxycarbonyl.

A third group of preferred compounds of Formula IA are those compounds wherein
   $R_1$ is 5-halo, 5-methyl, 5-cyano or trifluoromethyl;
   $R_{10}$ and $R_{11}$ are each independently H or halo;
   A is —C(H)=;
   $R_2$ and $R_3$ are H;
   $R_4$ is H, methyl or phenyl($C_1$–$C_2$)alkyl, wherein said phenyl groups are mono- or di-substituted independently with H, halo, ($C_1$–$C_4$)alkyl, ($C_1$–$C_4$)alkoxy, trifluoromethyl, hydroxy, amino or cyano and wherein said phenyl groups are additionally mono- or di-substituted independently H or halo; or
   $R_4$ is thien-2- or -3-yl($C_1$–$C_2$)alkyl, pyrid-2-, -3- or -4-yl ($C_1$–$C_2$)alkyl, thiazol-2-, -4- or -5-yl($C_1$–$C_2$)alkyl, imidazol-2-, -4- or -5-yl($C_1$–$C_2$)alkyl, fur-2- or -3-yl ($C_1$–$C_2$)alkyl, pyrrol-2- or -3-yl($C_1$–$C_2$)alkyl, oxazol-2-, -4- or -5-yl($C_1$–$C_2$)alkyl, pyrazol-3-, -4- or -5-yl ($C_1$–$C_2$)alkyl, isoxazol-3-, -4- or -5-yl($C_1$–$C_2$)alkyl, isothiazol-3-, -4- or -5-yl($C_1$–$C_2$)alkyl,pyridazin-3- or -4-yl($C_1$–$C_2$)alkyl, pyrimidin-2-, -4-, -5- or -6-yl ($C_1$–$C_2$)alkyl, pyrazin-2- or -3-yl($C_1$–$C_2$)alkyl or 1,3, 5-triazin-2-yl($C_1$–$C_2$)alkyl wherein said preceding $R_4$ heterocycles are optionally mono- or di-substituted independently with halo, trifluoromethyl, ($C_1$–$C_4$) alkyl, ($C_1$–$C_4$)alkoxy, amino or hydroxy and said mono- or di-substituents are bonded to carbon;
   $R_5$ is H; and
   $R_6$ is carboxy.

Within the third group of preferred compounds is a first group of especially preferred compounds wherein
   $R_{10}$ and $R_{11}$ are H; and
   $R_4$ is H.

Particularly preferred within the immediately preceding especially preferred group is a compound wherein
   $R_1$ is 5-chloro.

Another group of preferred glycogen phosphorylase inhibitors includes:

5-chloro-1H-indole-2-carboxylic acid [(1S)-((R)-hydroxy-dimethylcarbamoyl-methyl)-2-phenyl-ethyl]-amide;

5-chloro-1H-indole-2-carboxylic acid [(1S)-((R)-hydroxy-(methoxy-methyl-carbamoyl)-methyl)-2-phenyl-ethyl]-amide;

5-chloro-1H-indole-2-carboxylic acid [(1S)-benzyl-3-((3-hydroxy azetidin-1-yl)-(2R)-hydroxy-3-oxopropyl]-amide;

5-chloro-1H-indole-2-carboxylic acid [(1S)-((R)-hydroxy-[methyl-(2-hydroxyethyl)-carbamoyl]-methyl)-2-phenyl-ethyl]-amide;

5-chloro-1H-indole-2-carboxylic acid [(1S)-benzyl-(2R)-hydroxy-3-((3S)-hydroxy-pyrrolidin-1-yl)-3-oxopropyl]-amide;

5-chloro-1H-indole-2-carboxylic acid [(1S)-benzyl-(2R)-hydroxy -3-((3S,4S)-dihydroxy-pyrrolidin-1-yl)-3-oxopropyl]-amide;

5-chloro-1H-indole-2-carboxylic acid [(1S)-benzyl-3-(cis-3,4-dihydroxy-pyrrolidin-1-yl)-(2R)-hydroxy-3-oxoprepyl]-amide;

5-chloro-1H-indole-2-carboxylic acid [1-benzyl-2-(3-hydroxypyrrolidin-1-yl)-2-oxo-ethyl]-amide;

5-chloro-1H-indole-2-carboxylic acid [(1S)-benzyl-2-(cis-3,4-dihydroxypyrrolidin-1-yl)-2-oxo-ethyl]-amide;

5-chloro-1H-indole-2-carboxylic acid [(1S)-(4-fluorobenzyl-2-(4-hydroxy-piperidin-1-yl)-2-oxo-ethyl]-amide;

5-chloro-1H-indole-2-carboxylic acid (2-oxo-2-thiazolidin-3-yl-ethyl)-amide;

5-chloro-1H-indole-2-carboxylic acid [(1S)-benzyl-2-(3-hydroxy-azetidin-1-yl)-2-oxo-ethyl]-amide;

5-chloro-1H-indole-2-carboxylic acid [(1S)-benzyl-2-(3-hydroxyimino-azetidin-1-yl)-2-oxo-ethyl]-amide; and 5-chloro-1H-indole-2-carboxylic acid [(1S)-benzyl-2-((3S,4S)-dihydroxy-pyrrolidin-1-yl)-2-oxo-ethyl]-amide, and the pharmaceutically acceptable salts, and prodrugs and salts of the prodrugs.

Any glycogen phosphorylase inhibitor may be used as a compound (active agent) in the present invention. Glycogen phosphorylase inhibition is readily determined by those skilled in the art according to standard assays (for example, Pesce, et al. (1977) *Clinical Chemistry* 23:1711–1717). A variety of glycogen phosphorylase inhibitors are described above, however, other glycogen phosphorylase inhibitors will be known to those skilled in the art (e.g., WO 95/24391-A and those disclosed in U.S. Pat. No. 5,952,363). The following documents also disclose glycogen phosphorylase inhibitors that can be used in the present invention: U.S. Pat. No. 5,998,463; Oikanomakos et al., *Protein Science*, 1999 8(10) 1930–1945, which in particular discloses the compound 3-isopropyl-4-(2-chlorophenyl)-1,4-dihydro-1-ethyl-2-methylpyridine; WO 9524391; WO 9709040; WO 9840353; WO 9850359; WO 9731901; EP 884050; and Hoover et al., *J. Med. Chem.*, 1998, 41, 2934–2938.

A glycogen phosphorylase inhibitor is administered to a patient in a therapeutically effective amount. The glycogen phosphorylase inhibitor can be administered alone or as part of a pharmaceutically acceptable composition or formulation. In addition, the glycogen phosphorylase inhibitor or composition can be administered all at once, as for example, by a bolus injection, multiple times, such as by a series of tablets, or delivered substantially uniformly over a period of time, as for example, using transdermal delivery. It is also noted that the dose of the glycogen phosphorylase inhibitor can be varied over time.

In addition, a glycogen phosphorylase inhibitor can be administered alone, in combination with other glycogen phosphorylase inhibitors, or in combination with other pharmaceutically active compounds. The other pharmaceutically active compounds can be intended to treat the same disease or condition as the glycogen phosphorylase inhibitor or a different disease or condition. If the patient is to receive or is receiving multiple pharmaceutically active compounds, the compounds can be administered simultaneously, or sequentially. For example, in the case of tablets, the active compounds may be found in one tablet or in separate tablets, which can be administered at once or sequentially in any order. In addition, it should be recognized that the compositions may be different forms. For example, one or more compounds may be delivered via a tablet, while another is administered via injection or orally as a syrup. All combinations, delivery methods and administration sequences are contemplated.

Since one aspect of the present invention contemplates the treatment of the disclosed diseases/conditions with a combination of pharmaceutically active agents that may be administered separately in any order, the invention further relates to combining separate pharmaceutical compositions in kit form. The kit comprises two separate pharmaceutical compositions: a glycogen phosphorylase inhibitor, and a second pharmaceutical compound. The kit comprises a container for containing the separate compositions such as a divided bottle or a divided foil packet. Additional examples of containers include syringes, boxes, bags, and the like. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil, which is opposite from the direction in which the recesses were formed. As a result, the tablets or capsules are sealed in the recesses between the plastic foil and the sheet. Preferably, the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several pills or capsules to be taken on a given day. Also, a daily dose of a glycogen phosphorylase inhibitor can consist of one tablet or capsule, while a daily dose of the second compound can consist of several tablets or capsules and vice versa. The memory aid should reflect this and aid in correct administration of the active agents.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter that indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

A glycogen phosphorylase inhibitor and other pharmaceutically active agents, if desired, can be administered to a patient either orally, rectally, parenterally, (for example, intravenously, intramuscularly, or subcutaneously) intracisternally, intravaginally, intraperitoneally, intravesically, locally (for example, powders, ointments or drops), or as a buccal or nasal spray.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Microorganism contamination can be prevented by adding various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (e) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, and tablets, the dosage forms may also comprise buffering agents.

Solid compositions of a similar type may also be used as fillers in soft and hard filled gelatin capsules using such excipients as lactose or milk sugar, as well as high molecular weight polyethylene glycols, and the like.

Solid dosage forms such as tablets, dragees, capsules, pills, and granules can be prepared with coatings and shells, such as enteric coatings and others well known in the art. They may also contain opacifying agents, and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compound or compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents.

Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal or vaginal administration are preferably suppositories, which can be prepared by mixing the compound or compounds of the present invention with suitable non-irritating excipients or carriers such as cocoa butter, polyethylene glycol or a suppository wax, which are solid at ordinary room temperature, but liquid at body temperature, and therefore, melt in the rectum or vaginal cavity and release the active component.

Dosage forms for topical administration of a glycogen phosphorylase inhibitor include ointments, powders, sprays and inhalants. The active compound or compounds are admixed under sterile conditions with a physiologically acceptable carrier, and any preservatives, buffers, or propellants that may be required. Opthalmic formulations, eye ointments, powders, and solutions are also contemplated as being within the scope of this invention.

The glycogen phosphorylase inhibitors of the present invention can be administered to a patient at dosage levels in the range of about 0.7 to about 7,000 mg per day. For a normal adult human having a body weight of about 70 kg, a dosage in the range of about 0.01 to about 100 mg per kilogram body weight is typically sufficient. The specific dosage and dosage range that can be used depends on a number of factors, including the requirements of the patient, the severity of the condition or disease being treated, and the pharmacological activity of the compound being administered. The determination of dosage ranges and optimal dosages for a particular patient is well within the ordinary skill in the art in light of this disclosure.

The following paragraphs describe exemplary formulations, dosages etc. useful for non-human animals. The administration of a glycogen phosphorylase inhibitor can be effected orally or non-orally, for example by injection. An amount of a compound is administered such that an effective dose is received, generally a daily dose which, when administered orally to an animal is usually between 0.01 and 100 mg/kg of body weight, preferably between 0.1 and 50 mg/kg of body weight. Conveniently, the medication can be carried in the drinking water so that a therapeutic dosage of the agent is ingested with the daily water supply. The agent can be directly metered into drinking water, preferably in the form of a liquid, water-soluble concentrate (such as an aqueous solution of a water soluble salt). Conveniently, the active ingredient can also be added directly to the feed, as such, or in the form of an animal feed supplement, also referred to as a premix or concentrate. A premix or concentrate of a therapeutic agent in a carrier is more commonly employed for the inclusion of the agent in the feed. Suitable carriers are liquid or solid, as desired, such as water, various meals such as alfalfa meal, soybean meal, cottonseed oil meal, linseed oil meal, corncob meal and corn meal, molasses, urea, bone meal, and mineral mixes such as are commonly employed in poultry feeds. A particularly effective carrier is the respective animal feed itself; that is, a small portion of such feed. The carrier facilitates uniform distribution of the active materials in the finished feed with which the premix is blended. It is important that the compound be thoroughly blended into the premix and, subsequently, the feed. In this respect, the agent may be dispersed or dissolved in a suitable oily vehicle such as soybean oil, corn oil, cottonseed oil, and the like, or in a volatile organic solvent and then blended with the carrier. It will be appreciated that the proportions of active material in the concentrate are capable of wide variation since the amount of agent in the finished feed may be adjusted by blending the appropriate proportion of premix with the feed to obtain a desired level of therapeutic agent.

High potency concentrates may be blended by the feed manufacturer with a proteinaceous carrier such as soybean oil meal and other meals, as described above, to produce concentrated supplements, which are suitable for direct feeding to animals. In such instances, the animals are permitted to consume the usual diet. Alternatively, such concentrated supplements may be added directly to the feed to produce a nutritionally balanced, finished feed containing a therapeutically effective level of a compound according to the invention. The mixtures are thoroughly blended by standard procedures, such as in a twin shell blender, to ensure homogeneity.

If the supplement is used as a top dressing for the feed, it likewise helps to ensure uniformity of distribution of the active material across the top of the dressed feed.

Preferred medicated swine, cattle, sheep and goat feeds generally contain from about 1 to about 400 grams of active ingredient per ton of feed, the optimum amount for these animals usually being about 50 to about 300 grams per ton of feed.

Preferred poultry and domestic pet feeds usually contain about 1 to about 400 grams and preferably about 10 to about 400 grams of active ingredient per ton of feed.

For parenteral administration in animals, a glycogen phosphorylase inhibitor may be prepared in the form of a paste or a pellet and administered as an implant, usually under the skin of the head or ear of the animal.

In general, parenteral administration involves injection of a sufficient amount of a glycogen phosphorylase inhibitor to provide the animal with about 0.01 to about 100 mg/kg/day of body weight of the active ingredient. The preferred dosage for poultry, swine, cattle, sheep, goats and domestic pets is in the range of from about 0.1 to about 50 mg/kg/day.

Paste formulations can be prepared by dispersing the active compound in a pharmaceutically acceptable oil such as peanut oil, sesame oil, corn oil, or the like.

Pellets containing an effective amount of a glycogen phosphorylase inhibitor can be prepared by admixing a glycogen phosphorylase inhibitor with a diluent such as carbowax, carnauba wax, and the like, and a lubricant, such as magnesium or calcium stearate, can be added to improve the pelleting process.

It is recognized that more than one pellet may be administered to an animal to achieve the desired dose level. Moreover, it has been found that implants may also be made periodically during the animal treatment period in order to maintain the proper active agent in the level animal's body.

The term pharmaceutically acceptable salts, esters, amides, or prodrugs means the carboxylate salts, amino acid addition salts, esters, amides, and prodrugs of a glycogen phosphorylase inhibitor that are, within the scope of sound medical judgment, suitable for use with patients without undue toxicity, irritation, allergic response, and the like, commensurate with a reasonable benefit/risk ratio, and effective for their intended use, as well as the zwitterionic forms, where possible, of a glycogen phosphorylase inhibitor.

The term "salts" refers to inorganic and organic salts of a glycogen phosphorylase inhibitor. The salts can be prepared in situ during the final isolation and purification of a compound, or by separately reacting a compound with a suitable organic or inorganic acid and isolating the salt thus formed. Representative salts include the hydrobromide, hydrochloride, sulfate, bisulfate, nitrate, acetate, oxalate, palmitiate, stearate, laurate, borate, benzoate, lactate, phosphate, tosylate, citrate, besylate, maleate, fumarate, succinate, tartrate, naphthylate, mesylate, glucoheptonate, lactobionate, and laurylsulphonate salts, and the like. The salts may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, for example, S. M. Berge, et al., "Pharmaceutical Salts," *J Pharm Sci*, 66: 1–19 (1977).

Examples of pharmaceutically acceptable, non-toxic esters of a glycogen phosphorylase inhibitor, if applicable, include $C_1$–$C_8$alkyl esters. Acceptable esters also include $C_5$–$C_7$cycloalkyl esters, as well as arylalkyl esters such as benzyl. $C_1$–$C_4$ alkyl esters are preferred. Esters of a glycogen phosphorylase inhibitor may be prepared according to methods that are well known in the art.

Examples of pharmaceutically acceptable non-toxic amides of a glycogen phosphorylase inhibitor include amides derived from ammonia, primary $C_1$–$C_8$alkyl amines, and secondary $C_1$–$C_8$dialkyl amines. In the case of secondary amines, the amine may also be in the form of a 5 or 6 membered heterocycloalkyl group containing at least one nitrogen atom. Amides derived from ammonia, $C_1$–$C_3$ primary alkyl amines, and $C_1$–$C_2$ dialkyl secondary amines are preferred. Amides of a glycogen phosphorylase inhibitor may be prepared according to methods well known to those skilled in the art.

The term "prodrug" means a compound that is transformed in vivo to yield a glycogen phosphorylase inhibitor. The transformation may occur by various mechanisms, such as through hydrolysis in blood. A discussion of the use of prodrugs is provided by T. Higuchi and W. Stella, "Prodrugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987.

For example, if a glycogen phosphorylase inhibitor contains a carboxylic acid functional group, a prodrug can comprise an ester formed by the replacement of the hydrogen atom of the acid group with a group such as ($C_1$–$C_8$) alkyl, ($C_2$–$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N—($C_1$–$C_2$)alkylamino($C_2$–$C_3$)alkyl (such as β-dimethylaminoethyl), carbamoyl-($C_1$–$C_2$)alkyl, N,N-di ($C_1$–$C_2$)alkylcarbamoyl-($C_1$–$C_2$)alkyl and piperidino-, pyrrolidino- or morpholino($C_2$–$C_3$)alkyl.

Similarly, if a glycogen phosphorylase inhibitor comprises an alcohol functional group, a prodrug can be formed by the replacement of the hydrogen atom of the alcohol group with a group such as ($C_1$–$C_6$)alkanoyloxymethyl, 1-(($C_1$–$C_6$)alkanoyloxy)ethyl, 1-methyl-1-(($C_1$–$C_6$) alkanoyloxy)ethyl, ($C_1$–$C_6$)alkoxycarbonyloxymethyl, N—($C_1$–$C_6$)alkoxycarbonylaminomethyl, succinoyl, ($C_1$–$C_6$)alkanoyl, α-amino($C_1$–$C_4$)alkanoyl, arylacyl and α-aminoacyl, or α-aminoacyl-α-aminoacyl, where each α-aminoacyl group is independently selected from the naturally occurring L-amino acids, P(O)(OH)$_2$, —P(O)(O ($C_1$–$C_6$)alkyl)$_2$ or glycosyl (the radical resulting from the removal of a hydroxyl group of the hemiacetal form of a carbohydrate).

If a glycogen phosphorylase inhibitor comprises an amine functional group, a prodrug can be formed by the replacement of a hydrogen atom in the amine group with a group such as R-carbonyl, RO-carbonyl, NRR'-carbonyl where R and R' are each independently (($C_1$–$C_{10}$)alkyl, ($C_3$–$C_7$) cycloalkyl, benzyl, or R-carbonyl is a natural α-aminoacyl or natural α-aminoacyl-natural α-aminoacyl, —C(OH)C(O) OY wherein (Y is H, ($C_1$–$C_6$)alkyl or benzyl), —C(OY$_0$)Y$_1$ wherein Y$_0$ is ($C_1$–$C_4$) alkyl and Y$_1$ is (($C_1$–$C_6$)alkyl, carboxy($C_1$–$C_6$)alkyl, amino($C_1$–$C_4$)alkyl or mono-N— or di-N,N—($C_1$–$C_6$)alkylaminoalkyl, —C(Y$_2$)Y$_3$ wherein Y$_2$ is H or methyl and Y$_3$ is mono-N— or di-N,N—($C_1$–$C_6$) alkylamino, morpholino, piperidin-1-yl or pyrrolidin-1-yl.

A glycogen phosphorylase inhibitor may contain asymmetric or chiral centers, and therefore, exist in different stereoisomeric forms. It is contemplated that all stereoisomeric forms of a glycogen phosphorylase inhibitor as well as mixtures thereof, including racemic mixtures, form part of the present invention. In addition, the present invention contemplates all geometric and positional isomers. For example, if a glycogen phosphorylase inhibitor contains a double bond, both the cis and trans forms, as well as mixtures, are contemplated.

Diasteromeric mixtures can be separated into their individual stereochemical components on the basis of their physical chemical differences by well known methods known such as chromatography and/or fractional crystallization. Enantiomers can be separated by converting the enantiomeric mixture into a diasteromeric mixture by reaction with an appropriate optically active compound (e.g., alcohol), separating the diastereomers and converting (e.g., hydrolyzing) the individual diastereomers to the corresponding pure enantiomers. Also, some of the glycogen phosphorylase inhibitors of this invention may be atropisomers (e.g., substituted biaryls) and are considered as part of the invention.

A glycogen phosphorylase inhibitor may exist in unsolvated as well as solvated forms with pharmaceutically acceptable solvents such as water, ethanol, and the like. The present invention contemplates and encompasses both the solvated and unsolvated forms.

It is also possible that a glycogen phosphorylase inhibitor may exist in different tautomeric forms. All tautomers of a glycogen phosphorylase inhibitor are contemplated. For example, all of the tautomeric forms of the imidazole moiety are included in the invention. Also, for example, all keto-enol or imine-enamine forms of the compounds are included in the invention.

Those skilled in the art will recognize that the compound names contained herein may be based on a particular tautomer of a compound. While the name for only a particular tautomer may be used, it is intended that all tautomers are encompassed by the name of the particular tautomer and included as part of the invention.

It is also intended that the invention disclosed herein encompass compounds that are synthesized in vitro using laboratory techniques, such as those well known to synthetic chemists; or synthesized using in vivo techniques, such as through metabolism, fermentation, digestion, and the like. It is also contemplated that the compounds of the present invention may be synthesized using a combination of in vitro and in vivo techniques.

The present invention also includes isotopically-labelled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Glycogen phosphorylase inhibitors that contain the aforementioned isotopes and/or other isotopes of other atoms are within the scope of this invention. Certain isotopically-labelled glycogen phosphorylase inhibitors, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detection. Further, substitution with heavier isotopes such as deuterium, i.e.,$^{2}H$, can afford certain therapeutic advantages resulting from greater metabolic stability, for example increased in vivo half-life or reduced dosage requirements and, hence, may be preferred in some circumstances.

Representative agents that can be used in combination with a glycogen phosphorylase inhibitor include agents used to treat diabetes such as insulin and insulin analogs (e.g. LysPro insulin); GLP-1 (7–37) (insulinotropin) and GLP-1 (7–36)-$NH_2$; biguanides: metformin, phenformin, buformin; α2-antagonists and imidazolines: midaglizole, isaglidole, deriglidole, idazoxan, efaroxan, fluparoxan; sulfonylureas and analogs: chlorpropamide, glibenclamide, tolbutamide, tolazamide, acetohexamide, glypizide, glimepiride, repaglinide, meglitinide; other insulin secretagogues: linogliride, A-4166; glitazones: ciglitazone, pioglitazone, englitazone, troglitazone, darglitazone, rosiglitazone; PPAR-gamma agonists; fatty acid oxidation inhibitors: clomoxir, etomoxir; α-glucosidase inhibitors: acarbose, miglitol, emiglitate, voglibose, MDL-25,637, camiglibose, MDL-73,945; , β-agonists: BRL 35135, BRL 37344, Ro 16-8714, ICI D7114, CL 316,243; phosphodiesterase inhibitors: L-386,398; lipid-lowering agents: benfluorex; antiobesity agents: fenfluramine; vanadate and vanadium complexes (e.g. Naglivan®)) and peroxovanadium complexes; amylin antagonists; glucagon antagonists; gluconeogenesis inhibitors; somatostatin analogs and antagonists; antilipolytic agents: nicotinic acid, acipimox, WAG 994. Also contemplated for use in combination with a glycogen phosphorylase inhibitor are pramlintide acetate (Symlin™), AC2993, and nateglinide. Any combination of agents can be administered as described above.

A glycogen phosphorylase inhibitor can also be used in combination with an aldose reductase inhibitor. Aldose reductase inhibitors constitute a class of compounds that have become widely known for their utility in treating conditions arising from complications of diabetes, such as diabetic neuropathy and nephropathy. Such compounds are well known to those skilled in the art and are readily identified by standard biological tests. For example, the aldose reductase inhibitor zopolrestat, 1-phthalazineacetic acid, 3,4-dihydro-4-oxo-3-[[5-(trifluoromethyl)-2-benzothiazolyl]methyl]-, and related compounds are described in U.S. Pat. No. 4,939,140 to Larson et al.

Aldose reductase inhibitors have been taught for use in lowering lipid levels in mammals. See, for example, U.S. Pat. No. 4,492,706 to Kallai-sanfacon and EP 0 310 931 A2 (Ethyl Corporation).

U.S. Pat. No. 5,064,830 to Going discloses the use of certain oxophthalazinyl acetic acid aldose reductase inhibitors, including zopolrestat, for lowering of blood uric acid levels.

Commonly assigned U.S. Pat. No. 5,391,551 discloses the use of certain aldose reductase inhibitors, including zopoirestat, for lowering blood lipid levels in humans. The disclosure teaches that therapeutic utilities derive from the treatment of diseases caused by an increased level of triglycerides in the blood, such diseases include cardiovascular disorders such as thrombosis, arteriosclerosis, myocardial infarction, and angina pectoris. A preferred aldose reductase inhibitor is zopolrestat.

The term aldose reductase inhibitor refers to compounds that inhibit the bioconversion of glucose to sorbitol, which is catalyzed by the enzyme aldose reductase.

Any aldose reductase inhibitor may be used in a combination with a glycogen phosphorylase inhibitor. Aldose reductase inhibition is readily determined by those skilled in the art according to standard assays (J. Malone, *Diabetes*, 29:861–864 (1980) "Red Cell Sorbitol, an Indicator of Diabetic Control"). A variety of aldose reductase inhibitors are described herein; however, other aldose reductase inhibitors useful in the compositions and methods of this invention will be known to those skilled in the art.

The activity of an aldose reductase inhibitor in a tissue can be determined by testing the amount of aldose reductase inhibitor that is required to lower tissue sorbitol (i.e., by inhibiting the further production of sorbitol consequent to blocking aldose reductase) or lower tissue fructose (by inhibiting the production of sorbitol consequent to blocking aldose reductase and consequently the production of fructose.

Accordingly, examples of aldose reductase inhibitors useful in the compositions, combinations and methods of the present invention include:

1. 3-(4-bromo-2-fluorobenzyl)-3,4-dihydro-4-oxo-1-phthalazineacetic acid (ponalrestat, U.S. Pat. No. 4,251,528);
2. N[[(5-trifluoromethyl)-6-methoxy-1-naphthalenyl]thioxomethyl]-N-methylglycine (tolrestat, U.S. Pat. No. 4,600,724);
3. 5-[(Z,E)-β-methylcinnamylidene]-4-oxo-2-thioxo-3-thiazolideneacetic acid (epalrestat, U.S. Pat. Nos. 4,464,382, 4,791,126, 4,831,045);
4. 3-(4-bromo-2-fluorobenzyl)-7-chloro-3,4-dihydro-2,4-dioxo-1(2H)-quinazolineacetic acid (zenarestat, U.S. Pat. Nos. 4,734,419, and 4,883,800);
5. 2R,4R-6,7-dichloro-4-hydroxy-2-methylchroman-4-acetic acid (U.S. Pat. No. 4,883,410);
6. 2R,4R-6,7-dichloro-6-fluoro-4-hydroxy-2-methylchroman-4-acetic acid (U.S. Pat. No. 4,883,410);
7. 3,4-dihydro-2,8-diisopropyl-3-oxo-2H-1,4-benzoxazine-4-acetic acid (U.S. Pat. No. 4,771,050);
8. 3,4-dihydro-3-oxo-4-[(4,5,7-trifluoro-2-benzothiazolyl)methyl]-2H-1,4-benzothiazine-2-acetic acid (SPR-210, U.S. Pat. No. 5,252,572);
9. N-[3,5-dimethyl-4-[(nitromethyl)sulfonyl]phenyl]-2-methyl-benzeneacetamide (ZD5522, U.S. Pat. Nos. 5,270,342 and 5,430,060);
10. (S)-6-fluorospiro[chroman-4,4'-imidazolidine]-2,5'-dione (sorbinil, U.S. Pat. No. 4,130,714);
11. d-2-methyl-6-fluoro-spiro(chroman-4',4'-imidazolidine)-2',5'-dione (U.S. Pat. No. 4,540,704);
12. 2-fluoro-spiro(9H-fluorene-9,4'-imidazolidine)2',5'-dione (U.S. Pat. No. 4,438,272);
13. 2,7-di-fluoro-spiro(9H-fluorene-9,4'-imidazolidine)2',5'-dione (U.S. Pat. Nos. 4,436,745, 4,438,272);
14. 2,7-di-fluoro-5-methoxy-spiro(9H-fluorene-9,4'-imidazolidine)2',5'-dione (U.S. Pat. Nos. 4,436,745, 4,438,272);
15. 7-fluoro-spiro(5H-indenol[1,2-b]pyridine-5,3'-pyrrolidine)2,5'-dione (U.S. Pat. Nos. 4,436,745, 4,438,272);
16. d-cis-6'-chloro-2',3'-dihydro-2'-methyl-spiro-(imidazolidine-4,4'-4'-H-pyrano(2,3-b)pyridine)-2,5-dione (U.S. Pat. No. 4,980,357);
17. spiro[imidazolidine-4,5'(6H)-quinoline]2,5-dione-3'-chloro-7',8'-dihydro-7'-methyl-(5'-cis)(U.S. Pat. No. 5,066,659);
18. (2S,4S)-6-fluoro-2',5'-dioxospiro(chroman4,4'-imidazolidine)-2-carboxamide (U.S. Pat. No. 5,447,946); and
19. 2-[(4-bromo-2-fluorophenyl)methyl]-6-fluorospiro[isoquinoline-4(1H),3'-pyrrolidine]-1,2',3,5'(2H)-tetrone (ARI-509, U.S. Pat. No. 5,037,831).

Other aldose reductase inhibitors include compounds having formula Ia below

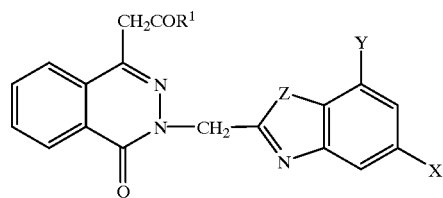

or a pharmaceutically acceptable salt or prodrug thereof, wherein

Z is O or S;

$R^1$ is hydroxy or a group capable of being removed in vivo to produce a compound of formula Ia wherein $R^1$ is OH; and X and Y are the same or different and are selected from hydrogen, trifluoromethyl, fluoro, and chloro.

A preferred subgroup within the above group of aldose reductase inhibitors includes numbered compounds 1, 2, 3, 4, 5, 6, 9, 10, and 17, and the following compounds of Formula Ia:

20. 3,4-dihydro-3-(5-fluorobenzothiazol-2-ylmethyl)-4-oxophthalazin-1-yl-acetic acid [$R^1$=hydroxy; X=F; Y=H];
21. 3-(5,7-difluorobenzothiazol-2-ylmethyl)-3,4-dihydro-4-oxophthalazin-1-ylacetic acid [$R^1$=hydroxy; X=Y=F];
22. 3-(5-chlorobenzothiazol-2-ylmethyl)-3,4-dihydro-4-oxophthalazin-1-ylacetic acid [$R^1$=hydroxy; X=Cl; Y=H];
23. 3-(5,7-dichlorobenzothiazol-2-ylmethyl)-3,4-dihydro-4-oxophthalazin-1-ylacetic acid [$R^1$=hydroxy; X=Y=Cl];
24. 3,4-dihydro-4-oxo-3-(5-trifluoromethylbenzoxazol-2-ylmethyl)phthalazin-1-ylacetic acid [$R^1$=hydroxy; X=CF$_3$; Y=H];
25. 3,4-dihydro-3-(5-fluorobenzoxazol-2-ylmethyl)-4-oxophthalazin-1-yl-acetic acid [$R^1$=hydroxy; X=F; Y=H];
26. 3-(5,7-difluorobenzoxazol-2-ylmethyl)-3,4-dihydro-4-oxophthalazin-1-ylacetic acid [$R^1$=hydroxy; X=Y=F];
27. 3-(5-chlorobenzoxazol-2-ylmethyl)-3,4-dihydro-4-oxophthalazin-1-ylacetic acid [$R^1$=hydroxy; X=Cl; Y=H];
28. 3-(5,7-dichlorobenzoxazol-2-ylmethyl)-3,4-dihydro-4-oxophthalazin-1-ylacetic acid [$R^1$=hydroxy; X=Y=Cl]; and
29. zopolrestat; 1-phthalazineacetic acid, 3,4-dihydro-4-oxo-3-[[5-(trifluoromethyl)-2-benzothiazolyl]methyl]-[$R^1$=hydroxy; X=trifluoromethyl; Y=H].

In compounds 20–23, and 29 Z is S. In compounds 24–28, Z is O.

Of the above subgroup, compounds 20–29 are more preferred with 29 especially preferred. Procedures for making the aldose reductase inhibitors of formula Ia are disclosed in PCT publication number WO 99/26659.

Each of the aldose reductase inhibitors referenced above and other aldose reductase inhibitors can be used in combination with one or more glycogen phosphorylase inhibitors to treat diabetic cardiomyopathy.

A glycogen phosphorylase inhibitor can also be used in combination with a sorbitol dehydrogenase inhibitor. Sorbitol dehydrogenase inhibitors lower fructose levels and have been used to treat or prevent diabetic complications such as neuropathy, retinopathy, nephropathy, cardiomyopathy, microangiopathy, and macroangiopathy. U.S. Pat. Nos. 5,728,704 and 5,866,578 disclose compounds and methods for treating diabetic complications by inhibiting the enzyme sorbitol dehydrogenase.

Each of the sorbitol dehydrogenase inhibitors referenced above and other sorbitol dehydrogenase inhibitors can be used in combination with one or more glycogen phosphorylase inhibitors to treat diabetic cardiomyopathy.

A glycogen phosphorylase inhibitor can also be used in combination with a glucocorticoid receptor antagonist. The glucocorticoid receptor (GR) is present in glucocorticoid responsive cells where it resides in the cytosol in an inactive state until it is stimulated by an agonist. Upon stimulation the glucocorticoid receptor translocates to the cell nucleus where it specifically interacts with DNA and/or protein(s) and regulates transcription in a glucocorticoid responsive manner. Two examples of proteins that interact with the glucocorticoid receptor are the transcription factors, API and NFκ-β. Such interactions result in inhibition of API- and NFκ-β-mediated transcription and are believed to be responsible for the anti-inflamatory activity of endogenously administered glucocorticoids. In addition, glucocorticoids may also exert physiologic effects independent of nuclear transcription. Biologically relevant glucocorticoid receptor agonists include cortisol and corticosterone. Many synthetic glucocorticoid receptor agonists exist including dexamethasone, prednisone and prednisilone. By definition, glucocorticoid receptor antagonists bind to the receptor and prevent glucocorticoid receptor agonists from binding and eliciting GR mediated events, including transcription. RU486 is an example of a non-selective glucocorticoid receptor antagonist. GR antagonists can be used in the treatment of diseases associated with an excess or a deficiency of glucocorticoids in the body. As such, they may be used to treat the following: obesity, diabetes, cardiovascular disease, hypertension, Syndrome X, depression, anxiety, glaucoma, human immunodeficiency virus (HIV) or acquired immunodeficiency syndrome (AIDS), neurodegeneration (for example, Alzheimer's and Parkinson's), cognition enhancement, Cushing's Syndrome, Addison's Disease, osteoporosis, frailty, inflammatory diseases (such as osteoarthritis, rheumatoid arthritis, asthma and rhinitis), tests of adrenal function, viral infection, immunodeficiency, immunomodulation, autoimmune diseases, allergies, wound healing, compulsive behavior, multi-drug resistance, addiction, psychosis, anorexia, cachexia, post-traumatic stress syndrome, post-surgical bone fracture, medical catabolism and prevention of muscle frailty.

Examples or GR antagonists that can be used in combination with a glycogen phosphorylase inhibitor include compounds of formula Ib below:

Ib an isomer thereof, a prodrug of said compound or isomer, or a pharmaceutically acceptable salt of said compound, isomer or prodrug; wherein m is 1 or 2;
- - - represents an optional bond;
A is selected from the group consisting of

A-1

A-2

A-3

A-4 and

A-5

A-5
D is $CR_7$, $CR_7R_{16}$, N, $NR_7$ or O;
E is C, $CR_6$ or N;
F is $CR_4$, $CR_4R_5$ or O;
G, H and I together with 2 carbon atoms from the A-ring or 2 carbon atoms from the B-ring form a 5-membered heterocyclic ring comprising one or more N, O or S atoms; provided that there is at most one of O and S per ring; J, K, L and M together with 2 carbon atoms from the B-ring forms a 6-membered heterocyclic ring comprising 1 or more N atoms;
X is a) absent, b) —$CH_2$—, c) —CH(OH)— or d) —C(O)—;
$R_1$ is a) —H, b) —Z—$CF_3$, c) —($C_1$-$C_6$)alkyl, d) —($C_2$-$C_6$)alkenyl, e) —($C_2$-$C_6$)alkynyl, f) —CHO, g) —CH=N—$OR_{12}$, h) —Z—C(O)$OR_{12}$, i) —Z—C(O)—$NR_{12}R_{13}$, j) —Z—C(O)—$NR_{12}$—Z-het, k) —Z—$NR_{12}R_{13}$, i) —Z—$NR_{12}$het, m) —Z-het, n) —Z—O-het, o) —Z-aryl', p) —Z—O-aryl', q) —CHOH-aryl' or r) —C(O)-aryl' wherein aryl' in substituents o) to r) is substituted independently with 0, 1 or 2 of the following: —Z—OH, —Z—NR$_{12}$R$_{13}$, —Z—NR$_{12}$-het, —C(O)NR$_{12}$R$_{13}$, —C(O)O(C$_1$–C$_6$) alkyl, —C(O)OH, —C(O)-het, —NR$_{12}$—C(O)—(C$_1$–C$_6$)alkyl, —NR$_{12}$—C(O)—(C$_2$–C$_6$)alkenyl, —NR$_{12}$—C(O)—(C$_2$–C$_6$)alkynyl, —NR$_{12}$—C(O)—Z-het, —CN, —Z-het, —O—(C$_1$–C$_3$)alkyl-C(O)—NR$_{12}$R$_{13}$, —O—(C$_1$–C$_3$)alkyl-C(O)O(C$_1$–C$_6$)alkyl, —NR$_{12}$—Z—C(O)O(C$_1$–C$_6$)alkyl, —N(Z—C(O)O(C$_1$–C$_6$)alkyl)$_2$, —NR$_{12}$—Z—C(O)—NR$_{12}$R$_{13}$, —Z—NR$_{12}$—SO$_2$—R$_{13}$, —NR$_{12}$-SO$_2$-het, —C(O)H, —Z—NR$_{12}$—Z—O(C$_1$–C$_6$)alkyl, —Z—NR$_{12}$—Z—NR$_{12}$R$_{13}$, —Z—NR$_{12}$—(C$_3$–C$_6$)cycloalkyl, —Z—N(Z—O(C$_1$–C$_6$)alkyl)$_2$, —SO$_2$E$_{12}$, —SOR$_{12}$, —SR$_{12}$, —SO$_2$NR$_{12}$R$_{13}$, —O—C(O)—(C$_1$–C$_4$)alkyl, —O—SO$_2$—(C$_1$–C$_4$)alkyl, -halo or —CF$_3$;

Z for each occurrence is independently a) —(C$_0$–C$_6$)alkyl, b) —(C$_2$–C$_6$)alkenyl or c) —(C$_2$–C$_6$)alkynyl;

R$_2$ is a) —H, b) -halo, c) —OH, d) —(C$_1$–C$_6$)alkyl substituted with 0 or 1 —OH, e) —NR$_{12}$R$_{13}$, f) —Z—C(O)O(C$_1$–C$_6$)alkyl, g) —Z—C(O)NR$_{12}$R$_{13}$, h) —O—(C$_1$–C$_6$)alkyl, i) —Z—O—C(O)—(C$_1$–C$_6$)alkyl, j) —Z—O—(C$_1$–C$_3$)alkyl-C(O)—NR$_{12}$R$_{13}$, k) —Z—O—(C$_1$–C$_3$)alkyl-C(O)—O(C$_1$–C$_6$)alkyl, l) —O—(C$_2$–C$_6$)alkenyl, m) —O—(C$_2$–C$_6$)alkynyl, n) —O—Z-het, o) —COOH, p) —C(OH)R$_{12}$R$_{13}$ or q) —Z—CN;

R$_3$ is a) —H, b) —(C$_1$–C$_{10}$)alkyl wherein 1 or 2 carbon atoms, other than the connecting carbon atom, may optionally be replaced with 1 or 2 heteroatoms independently selected from S, O and N and wherein each carbon atom is substituted with 0, 1 or 2 R$_y$, c) —(C$_2$–C$_{10}$)alkenyl substituted with 0, 1 or 2 R$_y$, d) —(C$_2$–C$_{10}$)alkynyl, wherein 1 carbon atom, other than the connecting carbon atom, may optionally be replaced with 1 oxygen atom and wherein each carbon atom is substituted with 0, 1 or 2 R$_y$, e) —CH=C=CH$_2$, f) —CN, g) —(C$_3$–C$_6$)cycloalkyl, h) —Z-aryl, i) —Z-het, j) —C(O)O(C$_1$–C$_6$)alkyl, k) —O(C$_1$–C$_6$)alkyl, l) —Z—S—R$_2$, m) —Z—S(O)—R$_{12}$, n) —Z—S(O)$_2$—R$_{12}$, o) —CF$_3$ p) —NR$_{12}$O—(C$_1$–C$_6$)alkyl or q) —CH$_2$OR$_y$;

provided that one of R$_2$ and R$_3$ is absent when there is a double bond between CR$_2$R$_3$ (the 7 position) and the F moiety (the 8 position) of the C-ring;

R$_y$ for each occurrence is independently a) —OH, b) -halo, c) —Z—CF$_3$, d) —Z—CF(C$_1$–C$_3$ alkyl)$_2$, e) —CN, f) —NR$_{12}$R$_{13}$, g) —(C$_3$–C$_6$)cycloalkyl, h) —(C$_3$–C$_6$)cycloalkenyl, i) —(C$_0$–C$_3$)alkyl-aryl, j) -het or k) —N$_3$;

or R$_2$ and R$_3$ are taken together to form a) =CHR$_{11}$, b) =NOR$_{11}$, c) =O, d) =N—NR$_{12}$, e) =N—NR$_{12}$—C(O)—R$_{12}$, f) oxiranyl or g) 1,3-dioxolan-4-yl;

R$_4$ and R$_5$ for each occurrence are independently a) —H, b) —CN, c) —(C$_1$–C$_6$)alkyl substituted with 0 to 3 halo, d) —(C$_2$–C$_6$)alkenyl substituted with 0 to 3 halo, e) —(C$_2$–C$_6$)alkynyl substituted with 0 to 3 halo, f) —O—(C$_1$–C$_6$)alkyl substituted with 0 to 3 halo, g) —O—(C$_2$–C$_6$)alkenyl substituted with 0 to 3 halo, h) —O—(C$_2$–C$_6$)alkynyl substituted with 0 to 3 halo, i) halo, j) —OH, k) (C$_3$–C$_6$)cycloalkyl or l) (C$_3$–C$_6$)cycloalkenyl;

or R$_4$ and R$_5$ are taken together to form =O;

R$_6$ is a) —H, b) —CN, c) —(C$_1$–C$_6$)alkyl substituted with 0 to 3 halo, d) —(C$_2$–C$_6$)alkenyl substituted with 0 to 3 halo, e) —(C$_2$–C$_6$)alkynyl substituted with 0 to 3 halo or f) —OH;

R$_7$ and R$_{16}$ for each occurrence are independently a) —H, b) -halo, c) —CN, d) —(C$_1$–C$_6$)alkyl substituted with 0 to 3 halo, e) —(C$_2$–C$_6$)alkenyl substituted with 0 to 3 halo or f) —(C$_2$–C$_6$)alkynyl substituted with 0 to 3 halo; provided that R$_7$ is other than —CN or -halo when D is NR$_7$;

or R$_7$ and R$_{16}$ are taken together to form =O;

R$_8$, R$_9$, R$_{14}$ and R$_{15}$ for each occurrence are independently a) —H, b) -halo, c) (C$_1$–C$_6$)alkyl substituted with 0 to 3 halo, d) —(C$_2$–C$_6$)alkenyl substituted with 0 to 3 halo, e) —(C$_2$–C$_6$)alkynyl substituted with 0 to 3 halo, f) —CN, g) —(C$_3$–C$_6$)cycloalkyl, h) —(C$_3$–C$_6$)cycloalkenyl, i) —OH, j) —O—(C$_1$–C$_6$)alkyl, k) —O—(C$_1$–C$_6$)alkenyl, l) —O—(C$_1$–C$_6$)alkynyl, m) —NR$_{12}$R$_{13}$, n) —C(O)OR$_{12}$ or o) —C(O)NR$_{12}$R$_{13}$;

or R$_8$ and R$_9$ are taken together on the C-ring to form =O; provided that when m is 2, only one set of R$_8$ and R$_9$ are taken together to form =O;

or R$_{14}$ and R$_{15}$ are taken together to form =O; provided that when R$_{14}$ and R$_{15}$ are taken together to form =O, D is other than CR$_7$ and E is other than C;

R$_{10}$ is a) —(C$_1$–C$_{10}$)alkyl substituted with 0 to 3 substituents independently selected from -halo, —OH and —N$_3$, b) —(C$_2$–C$_{10}$)alkenyl substituted with 0 to 3 substituents independently selected from -halo, —OH and —N$_3$, c) —(C$_2$–C$_{10}$)alkynyl substituted with 0 to 3 substituents independently selected from -halo, —OH and —N$_3$, d) -halo, e) —Z—CN, f) —OH, g) —Z-het, h) —Z—NR$_{12}$R$_{13}$, i) —Z—C(O)-het, j) —Z—C(O)—(C$_1$–C$_6$)alkyl, k) —Z—C(O)—NR$_{12}$R$_{13}$, l) —Z—C(O)—NR$_{12}$—Z—CN, m) —Z—C(O)—NR$_{12}$—Z-het, n) —Z—C(O)—NR$_{12}$—Z-aryl, o) —Z—C(O)—NR$_2$—Z—NR$_{12}$R$_{13}$, p) —Z—C(O)—NR$_{12}$—Z—O(C$_1$–C$_6$)alkyl, q) —(C$_1$–C$_6$)alkyl-C(O)OH, r) —Z—C(O)O(C$_1$–C$_6$)alkyl, s) —Z—O—(C$_0$–C$_6$)alkyl-het, t) —Z—O—(C$_0$–C$_6$)alkyl-aryl, u) —Z—O—(C$_1$–C$_6$)alkyl substituted with 0 to 2 R$_x$, v) —Z—O—(C$_1$–C$_6$)alkyl-CH(O), w) —Z—O—(C$_1$–C$_6$)alkyl-NR$_{12}$-het, x) —Z—O—Z-het-Z-het, y) —Z—O—Z-het-Z—NR$_{12}$R$_{13}$, z) —Z—O—Z-het-C(O)-het, a1) —Z—O—Z—C(O)-het, b1) —Z—O—Z—C(O)-het-het, c1) —Z—O—Z—C(O)—(C$_1$–C$_6$)alkyl, d1) —Z—O—Z—C(S)—NR$_{12}$R$_{13}$, e1) —Z—O—Z—C(O)—NR$_{12}$R$_{13}$, f1) —Z—O—Z—(C$_1$–C$_3$)alkyl-C(O)—NR$_{12}$R$_{13}$, g1) —Z—O—Z—C(O)—O(C$_1$–C$_6$)alkyl, h1) —Z—O—Z—C(O)—OH, i1) —Z—O—Z—C(O)—NR$_{12}$—O(C$_1$–C$_6$)alkyl, j1) —Z—O—Z—C(O)—NR$_{12}$—OH, k1) —Z—O—Z—C(O)—NR$_{12}$—Z—NR$_{12}$R$_{13}$, l1) —Z—O—Z—C(O)—NR$_{12}$—Z-het, m1) —Z—O—Z—C(O)—NR$_{12}$—SO$_2$—(C$_1$–C$_6$)alkyl, n1) —Z—O—Z—C(=NR$_{12}$)(NR$_{12}$R$_{13}$), o1) —Z—O—Z—C(=NOR$_{12}$)(NR$_{12}$R$_{13}$), p1) —Z—NR$_{12}$—C(O)—O—Z—NR$_{12}$R$_{13}$, q1) —Z—S—C(O)—NR$_{21}$E$_{13}$, r1) —Z—O—SO$_2$—(C$_1$–C$_6$)alkyl, s1) —Z—O—SO$_2$-aryl, t1) —Z—O—SO$_2$—NR$_{12}$R$_{13}$, u1) —Z—O—SO$_2$—CF$_3$, v1) —Z—NR$_{12}$C(O)OR$_{13}$ or w1) —Z—NR$_{12}$C(O)R$_{13}$;

or R$_9$ and R$_{10}$ are taken together on the moiety of formula A-5 to form a) =O or b) =NOR$_{12}$;

R$_{11}$ is a) —H, b) —(C$_1$–C$_5$)alkyl, c) —(C$_3$–C$_6$)cycloalkyl or d) —(C$_0$–C$_3$)alkyl-aryl;

R$_{12}$ and R$_{13}$ for each occurrence are each independently a) —H, b) —(C$_1$–C$_6$)alkyl wherein 1 or 2 carbon atoms, other than the connecting carbon atom, may optionally be replaced with 1 or 2 heteroatoms independently selected from S, O and N and wherein each carbon atom is substituted with 0 to 6 halo, c) —(C₂–C₆) alkenyl substituted with 0 to 6 halo or d) —(C₁–C₆) alkynyl wherein 1 carbon atom, other than the connecting carbon atom, may optionally be replaced with 1 oxygen atom and wherein each carbon atom is substituted with 0 to 6 halo;

or R₁₂ and R₁₃ are taken together with N to form het;

or R₆ and R₁₄ or R₁₅ are taken together to form 1,3-dioxolanyl;

aryl is a) phenyl substituted with 0 to 3 R$_x$, b) naphthyl substituted with 0 to 3 R$_x$ or c) biphenyl substituted with 0 to 3 R$_x$;

het is a 5-,6- or 7-membered saturated, partially saturated or unsaturated ring containing from one (1) to three (3) heteroatoms independently selected from the group consisting of nitrogen, oxygen and sulfur; and including any bicyclic group in which any of the above heterocyclic rings is fused to a benzene ring or another heterocycle; and the nitrogen may be in the oxidized state giving the N-oxide form; and substituted with 0 to 3 R$_x$;

R$_x$ for each occurrence is independently a) -halo, b) —OH, c) —(C₁–C₆)alkyl, d) —(C₂–C₆)alkenyl, e) —(C₂–C₆)alkynyl, f) —O(C₁–C₆)alkyl, g) —O(C₂–C₆)alkenyl, h) —O(C₂–C₆)alkynyl, i) —(C₀–C₆)alkyl-NR₁₂R₁₃, j) —C(O)—NR₁₂R₁₃, k) —Z—SO₂R₁₂, l) —Z—SOR₁₂, m) —Z—SR₁₂, n) —NR₁₂—SO₂R₁₃, o) —NR₁₂—C(O)—R₁₃, p) —NR₁₂—R₁₃, r) —CN, s) —CF₃, t) —C(O)(C₁–C₆)alkyl, u) =O, v) —Z—SO₂-phenyl or w) —Z—SO₂-het';

aryl' is phenyl, naphthyl or biphenyl;

het' is a 5-,6- or 7-membered saturated, partially saturated or unsaturated ring containing from one (1) to three (3) heteroatoms independently selected from the group consisting of nitrogen, oxygen and sulfur; and including any bicyclic group in which any of the above heterocyclic rings is fused to a benzene ring or another heterocycle;

provided that:

1) X—R₁ is other than hydrogen or methyl;

2) when R₉ and R₁₀ are substituents on the A-ring, they are other than mono- or di-methoxy;

3) when R₂ and R₃ are taken together to form =CHR₁₁ or =O wherein R₁₁ is —O(C₁–C₆)alkyl, then —X—R₁ is other than (C₁–C₄)alkyl;

4) when R₂ and R₃ taken together are C=O and R₉ is hydrogen on the A-ring; or when R₂ is hydroxy, R₃ is hydrogen and R₉ is hydrogen on the A-ring, then R₁₀ is other than —O—(C₁–C₆)alkyl or —O—CH₂-phenyl at the 2-position of the A-ring;

5) when X—R₁ is (C₁–C₄)alkyl, (C₂–C₄)alkenyl or (C₂–C₄)alkynyl, R₉ and R₁₀ are other than mono-hydroxy or =O, including the diol form thereof, when taken together; and 6) when X is absent, R₁ is other than a moiety containing a heteroatom independently selected from N, O or S directly attached to the juncture of the B-ring and the C-ring. (See U.S. Provisional Patent Application No. 60/132,130, filed Apr. 30, 1999.)

Each of the glucocorticoid receptor antagonists referenced above and other glucocorticoid receptor antagonists can be used in combination with a glycogen phosphorylase inhibitor to treat diabetic cardiomyopathy.

A glycogen phosphorylase inhibitor can also be used in combination with a sodium-hydrogen exchanger type 1 (NHE-1) inhibitor. Examples of NHE-1 inhibitors include a compound having the Formula Ic

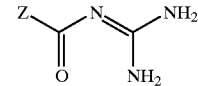

Formula Ic a prodrug thereof or a pharmaceutically acceptable salt of said compound or of said prodrug, wherein Z is carbon connected and is a five-membered, diaza, diunsaturated ring having two contiguous nitrogens, said ring optionally mono-, di-, or tri-substituted with up to three substituents independently selected from R¹, R² and R³; or Z is carbon connected and is a five-membered, triaza, diunsaturated ring, said ring optionally mono- or di-substituted with up to two substituents independently selected from R⁴ and R⁵;

wherein R¹, R², R³, R⁴ and R⁵ are each independently hydrogen, hydroxy(C₁–C₄)alkyl, (C₁–C₄)alkyl, (C₁–C₄)alkylthio, (C₃–C₄)cycloalkyl, (C₃–C₇)cycloalkyl(C₁–C₄)alkyl, (C₁–C₄)alkoxy, (C₁–C₄)alkoxy(C₁–C₄)alkyl, mono-N— or di-N,N—(C₁–C₄)alkylcarbamoyl, M or M(C₁–C₄)alkyl, any of said previous (C₁–C₄)alkyl moieties optionally having from one to nine fluorines; said (C₁–C₄)alkyl or (C₃–C₄)cycloalkyl optionally mono- or di-substituted independently with hydroxy, (C₁–C₄)alkoxy, (C₁–C₄)alkylthio, (C₁–C₄)alkylsulfinyl, (C₁–C₄)alkylsulfonyl, (C₁–C₄)alkyl, mono-N— or di-N,N—(C₁–C₄)alkylcarbamoyl or mono-N— or di-N,N—(C₁–C₄)alkylaminosulfonyl; and said (C₃–C₄)cycloalkyl optionally having from one to seven fluorines;

wherein M is a partially saturated, fully saturated or fully unsaturated five to eight membered ring optionally having one to three heteroatoms selected independently from oxygen, sulfur and nitrogen, or, a bicyclic ring consisting of two fused partially saturated, fully saturated or fully unsaturated three to six membered rings, taken independently, optionally having one to four heteroatoms selected independently from nitrogen, sulfur and oxygen;

said M is optionally substituted, on one ring if the moiety is monocyclic, or one or both rings if the moiety is bicyclic, on carbon or nitrogen with up to three substituents independently selected from R⁶, R⁷ and R⁸, wherein one of R⁶, R⁷ and R⁸ is optionally a partially saturated, fully saturated, or fully unsaturated three to seven membered ring optionally having one to three heteroatoms selected independently from oxygen, sulfur and nitrogen optionally substituted with (C₁–C₄)alkyl and additionally R⁶, R⁷ and R⁸ are optionally hydroxy, nitro, halo, (C₁–C₄)alkoxy, (C₁–C₄)alkoxycarbonyl, (C₁–C₄)alkyl, formyl, (C₁–C₄)alkanoyl, (C₁–C₄)alkanoyloxy, (C₁–C₄)alkanoylamino, (C₁–C₄)alkoxycarbonylamino, sulfonamido, (C₁–C₄)alkylsulfonamido, amino, mono-N— or di-N,N—(C₁–C₄)alkylamino, carbamoyl, mono-N— or di-N,N—(C₁–C₄)alkylcarbamoyl, cyano, thiol, (C₁–C₄)alkylthio, (C₁–C₄)alkylsulfinyl, (C₁–C₄)alkylsulfonyl, mono-N— or di-N,N—(C₁–C₄)alkylaminosulfonyl, (C₂–C₄)alkenyl, (C₂–C₄)alkynyl or (C₅–C₇)cycloalkenyl, wherein said (C₁–C₄)alkoxy, (C₁–C₄)alkyl, (C₁–C₇)alkanoyl, (C₁–C₄)alkylthio, mono-N— or di-N,N—

($C_1$-$C_4$)alkylamino or ($C_3$-$C_7$)cycloalkyl $R^6$, $R^7$ and $R^8$ substituents are optionally mono-substituted independently with hydroxy, ($C_1$-$C_4$)alkoxycarbonyl, ($C_3$-$C_7$)cycloalkyl, ($C_1$-$C_4$)alkanoyl, ($C_1$-$C_4$) alkanoylamino, ($C_1$-$C_4$)alkanoyloxy, ($C_1$-$C_4$) alkoxycarbonylamino, sulfonamido, ($C_1$-$C_4$) alkylsulfonamido, amino, mono-N— or di-N,N— ($C_1$-$C_4$)alkylamino, carbamoyl, mono-N— or di-N, N—($C_1$-$C_4$)alkylcarbamoyl, cyano, thiol, nitro, ($C_1$-$C_4$)alkylthio, ($C_1$-$C_4$)alkylsulfinyl, ($C_1$-$C_4$) alkylsulfonyl or mono-N— or di-N,N—($C_1$-$C_4$) alkylaminosulfonyl or optionally substituted with one to nine fluorines. (See PCT publication number WO 99/43663)

Each of the NHE-1 inhibitors referenced above and other NHE-1 inhibitors can be used in combination with a glycogen phosphorylase inhibitor to treat diabetic cardiomyopathy.

In addition, a glycogen phosphorylase inhibitor can be used in combination with a thyromimetic. It is generally accepted that thyroid hormones, specifically, biologically active iodothyronines, are critical to normal development and to maintaining metabolic homeostasis. Thyroid hormones stimulate the metabolism of cholesterol to bile acids and enhance the lipolytic responses of fat cells to other hormones. U.S. Pat. Nos. 4,766,121; 4,826,876; 4,910,305; and 5,061,798 disclose certain thyroid hormone mimetics (thyromimetics), namely, 3,5-dibromo-3'-[6-oxo-3(1H)-pyridazinylmethyl]-thyronines. U.S. Pat. No. 5,284,971 discloses certain thyromimetic cholesterol lowering agents, namely, 4-(3-cyclohexyl-4-hydroxy or -methoxy phenylsulfonyl)-3,5 dibromo-phenylacetic compounds. U.S. Pat. Nos. 5,401,772; 5,654,468; and 5,569,674 disclose certain thyromimetics that are lipid lowering agents, namely, heteroacetic acid derivatives. In addition, certain oxamic acid derivatives of thyroid hormones are known in the art. For example, N. Yokoyama, et al. in an article published in the *Journal of Medicinal Chemistry*, 38 (4): 695–707 (1995) describe replacing a —$CH_2$ group in a naturally occurring metabolite of $T_3$ with an —NH group resulting in —$HNCOCO_2H$. Likewise, R. E. Steele et al. in an article published in International Congressional Service (*Atherosclerosis* X) 1066: 321–324 (1995) and Z. F. Stephan et al. in an article published in *Atherosclerosis*, 126: 53–63 (1996), describe certain oxamic acid derivatives that are useful as lipid-lowering thyromimetic agents and are devoid of undesirable cardiac activities.

Each of the thyromimetic compounds referenced above and other thyromimetic compounds can be used in combination with one or more glycogen phosphorylase inhibitors to treat diabetic cardiomyopathy.

In another aspect of the present invention of treating diabetic cardiomyopathy, a glycogen phosphorylase inhibitor can be administered in combination with a compound that can be used to treat hypertension. Examples of classes of compounds that can be used to treat hypertension include calcium blockers, ACE inhibitors, diuretics, angiotensin II receptor blockers, β-blockers, and α-adrenergic blockers. In addition, combinations of compounds in the above-recited classes have been used to treat hypertension and these combinations of anti-hypertensive agents can be used in combination with one or more glycogen phosphorylase inhibitors. Examples of specific compounds used to treat hypertension that can be used in combination with a glycogen phosphorylase inhibitor to treat diabetic cardiomyopathy include Cardizem®, Adalat®, Calan®, Cardene®, Covera®, Dilacor®, DynaCirc®, Procardia XL®, Sular®, Tiazac®, Vascor®, Verelan®, Isoptin®, Nimotop®, Norvasc®, Plendil®, Accupril®, Altace®, Captopril®, Lotensin®, Mavik®, Monopril®, Prinivil®, Univasc®, Vasotec®, and Zestril®.

The examples presented below are intended to illustrate particular embodiments of the invention, and are not intended to limit the scope of the specification, including the claims, in any manner. All patents, patent applications, and other references cited in this application are hereby incorporated by reference.

EXAMPLES

The utility of the compounds of the present invention as medical agents in the treatment or prevention of diseases (such as are detailed herein) in animals, particularly mammals (e.g. humans) is demonstrated by the activity of the compounds in conventional assays and the in vitro and in vivo assays described below. Such assays also provide a means whereby the activities of the compounds can be compared with the activities of other known compounds. The results of these comparisons are useful for determining dosage levels in animals, particularly mammals, including humans, for the treatment of such diseases.

Glycogen Phosphorylase Production and Assays

The three different purified glycogen phosphorylase (GP) isoenzymes, wherein glycogen phosphorylase is in the activated "a" state (referred to as glycogen phosphorylase a, or the abbreviation GPa), and referred to here as human liver glycogen phosphorylase a (HLGPa), human muscle glycogen phosphorylase a (HMGPa), and human brain glycogen phosphorylase a (HBGPa), can be obtained by the following procedures.

Expression and Fermentation

The HLGP cDNAs (obtained as described in Newgard et al., *Proc. Natl. Acad. Sci.*, 83: 8132–8136 (1986), and Newgard et al., *Proc. Natl. Acad. Sci.*, 263: 3850–3857 (1988), respectively) and HMGP cDNAs (obtained by screening a Stratagene (Stratagene Cloning Systems, La Jolla, Calif.) human muscle cDNA library with a polymerase chain reaction (PCR)-generated cDNA fragment based on information and methodology reported for isolation of the human skeletal muscle glycogen phosphorylase gene and partial cDNA sequence by Kubisch et al., Center for Molecular Neurobiology, University of Hamburg, Martinisstrasse 85, Hamburg, 20246 Germany; Genbank (National Center for Biotechnology Information, National Institutes of Health, USA) Accession Numbers U94774, U94775, U94776 and U94777, submitted Mar. 20, 1997; Burke et al., *Proteins*, 2:177–187 (1987); and Hwang et al., *Eur. J. Biochem.*, 152: 267–274 (1985)) are expressed from plasmid pKK233-2 (Pharmacia Biotech. Inc., Piscataway, N.J.) in *E. coli* strain XL-1 Blue (Stratagene Cloning Systems, LaJolla, Calif.). The strain is inoculated into LB medium (consisting of 10 g tryptone, 5 g yeast extract, 5 g NaCl, and 1 ml 1N NaOH per liter) plus 100 mg/L ampicillin, 100 mg/L pyridoxine and 600 mg/L $MnCl_2$ and grown at 37° C. to a cell density of $OD_{550}$=1.0. At this point, the cells are induced with 1 mM isopropyl-1-thio-β-D-galactoside (IPTG). Three hours after induction the cells are harvested by centrifugation and cell pellets are frozen at −70° C. until needed for purification.

The HBGP cDNA can be expressed by several methodologies, for example, by the method described by Crerar, et al. (*J. Biol. Chem.* 270:13748–13756 (1995)). The method described by Crerar, et al. (*J. Biol. Chem.*, 270:13748–13756 (1995)) for the expression of HBGP is as follows: the HBGP cDNA can be expressed from plasmid pTACTAC in *E. coli* strain 25A6. The strain is inoculated into LB medium (consisting of 10 g tryptone, 5 g yeast extract, 5 g NaCl, and 1 ml 1N NaOH per liter) plus 50 mg/L ampicillin and grown overnight, then resuspended in fresh LB medium plus 50 mg/L ampicillin, and reinoculated into a 40× volume of LB/amp media containing 250 µM isopropyl-1-thio-β-D-galactoside (IPTG), 0.5 mM pyridoxine and 3 mM $MnCl_2$ and grown at 22° C. for 48–50 hours. The cells can then be harvested by centrifugation and cell pellets are frozen at −70° C. until needed for purification.

The HLGP cDNA is expressed from plasmid pBlueBac III (Invitrogen Corp., San Diego, Calif.) which is cotransfected with BaculoGold Linear Viral DNA (Pharmingen, San Diego, Calif.) into Sf9 cells. Recombinant virus is subsequently plaque-purified. For production of protein, Sf9 cells grown in serum-free medium (Sf-900 II serum free medium, Gibco BRL, Life Technologies, Grand Island, N.Y.) are infected at an moi of 0.5 and at a cell density of $2 \times 10^6$ cells/ml. After growth for 72 hours at 27° C., cells are centrifuged, and the cell pellets frozen at −70° C. until needed for purification.

Purification of Glycogen Phosphorylase expressed in *E. coli*

The *E. coli* cells in pellets described above are resuspended in 25 mM β-glycerophosphate (pH 7.0) with 0.2 mM DTT, 1 mM $MgCl_2$, plus the following protease inhibitors:

| | |
|---|---|
| 0.7 µg/ml | Pepstatin A |
| 0.5 µg/ml | Leupeptin |
| 0.2 mM | phenylmethylsulfonyl fluoride (PMSF), and |
| 0.5 mM | EDTA, | lysed by pretreatment with 200 µg/ml lysozyme and 3 µg/ml DNAase followed by sonication in 250 ml batches for 5×1.5 minutes on ice using a Branson Model 450 ultrasonic cell disrupter (Branson Sonic Power Co., Danbury Conn.). The *E. coli* cell lysates are then cleared by centrifugation at 35,000×g for one hour followed by filtration through 0.45 micron filters. GP in the soluble fraction of the lysates (estimated to be less than 1% of the total protein) is purified by monitoring the enzyme activity (as described in GPa Activity Assay section, below) from a series of chromatographic steps detailed below.

Immobilized Metal Affinity Chromatography (IMAC)

This step is based on the method of Luong et al (Luong et al. *Journal of Chromatography* 584: 77–84 (1992)). Five hundred ml of the filtered soluble fraction of cell lysates (prepared from approximately 160–250 g of original cell pellet) are loaded onto a 130 ml column of IMAC Chelating-Sepharose (Pharmacia LKB Biotechnology, Piscataway, N.J.) which has been charged with 50 mM $CuCl_2$ and 25 mM β-glycerophosphate, 250 mM NaCl and 1 mM imidazole at pH 7 (equilibration buffer). The column is washed with equilibration buffer until the $A_{280}$ returns to baseline. The sample is then eluted from the column with the same buffer containing 100 mM imidazole to remove the bound GP and other bound proteins. Fractions containing the GP activity are pooled (approximately 600 ml), and ethylenediaminetetraacetic acid (EDTA), DL-dithiothreitol (DTT), phenylmethylsulfonyl fluoride (PMSF), leupeptin and pepstatin A are added to obtain 0.3 mM, 0.2 mM, 0.2 mM, 0.5 µg/ml and 0.7 µg/ml concentrations respectively. The pooled GP is desalted over a Sephadex G-25 column (Sigma Chemical Co., St. Louis, Miss.) equilibrated with 25 mM Tris-HCl (pH 7.3), 3 mM DTT buffer (Buffer A) to remove imidazole and is stored on ice and subjected to a second chromatographic step (below) if necessary.

5'-AMP-Sepharose Chromatography

The desalted pooled GP sample (approximately 600 mL) is next mixed with 70 ml of 5'-AMP Sepharose (Pharmacia LKB Biotechnology, Piscataway, N.J.) which has been equilibrated with Buffer A (see above). The mixture is gently agitated for one hour at 22° C. then packed into a column and washed with Buffer A until the $A_{280}$ returns to baseline. GP and other proteins are eluted from the column with 25 mM Tris-HCl, 0.2 mM DTT and 10 mM adenosine 5'-monophosphate (AMP) at pH 7.3 (Buffer B). GP-containing fractions are pooled following identification by determining enzyme activity described below and visualizing the Mr approximately 97 kdal GP protein band by sodium dodecyl sulfate polyacrylamide gel electrophoresis (SDS-PAGE) followed by silver staining (2D-silver Stain II "Daiichi Kit", Daiichi Pure Chemicals Co., LTD., Tokyo, Japan) and then pooled. The pooled GP is dialyzed into 25 mM β-glycerophosphate, 0.2 mM DTT, 0.3 mM EDTA, 200 mM NaCl, pH 7.0 buffer (Buffer C) and stored on ice until use.

Prior to use of the GP enzyme, the enzyme is converted from the inactive form as expressed in *E. coli* strain XL-1 Blue (designated GPb) (Stragene Cloning Systems, La Jolla, Calif.), to the active form (designated GPa) by the procedure described in Section (A) Activation of GP below.

Purification of Glycogen Phosphorylase Expressed in Sf9 Cells

The Sf9 cells in pellets described above are resuspended in 25 mM β-glycerophosphate (pH 7.0) with 0.2 mM DTT, 1 mM $MgCl_2$, plus the following protease inhibitors:

| | |
|---|---|
| 0.7 µg/ml | Pepstatin A |
| 0.5 µg/ml | Leupeptin |
| 0.2 mM | phenylmethylsulfonyl fluoride (PMSF), and |
| 0.5 mM | EDTA, | lysed by pretreatment with 3 µg/ml DNAase followed by sonication in batches for 3×1 minute on ice using a Branson Model 450 ultrasonic cell disrupter (Branson Sonic Power Co., Danbury Conn.). The Sf9 cell lysates are then cleared by centrifugation at 35,000×g for one hour followed by filtration through 0.45 micron filters. GP in the soluble fraction of the lysates (estimated to be 1.5% of the total protein) is purified by monitoring the enzyme activity (as described in GPa Activity Assay section, below) from a series of chromatographic steps detailed below.

Immobilized Metal Affinity Chromatography (IMAC)

Immobilized Metal Affinity Chromatography is performed as described in the section above. The pooled, desalted GP is then stored on ice until further processed.

Activation of GP

Before further chromatography, the fraction of inactive enzyme as expressed in Sf9 cells (designated GPb) is converted to the active form (designated GPa) by the following procedure described in Section (A) Activation of GP below.

Anion Exchange Chromatography

Following activation of the IMAC purified GPb to GPa by reaction with the immobilized phosphorylase kinase, as described below, the pooled GPa fractions are dialyzed against 25 mM Tris-HCl, pH 7.5, containing 0.5 mM DTT, 0.2 mM EDTA, 1.0 mM phenylmethylsulfonyl fluoride (PMSF), 1.0 µg/ml leupeptin and 1.0 µg/ml pepstatin A. The fraction is then loaded onto a MonoQ Anion Exchange Chromatography column (Pharmacia Biotech. Inc., Piscataway, N.J.). The column is washed with equilibration buffer until the $A_{280}$ returns to baseline. The sample is then eluted from the column with a linear gradient of 0–0.25 M NaCl to remove the bound GP and other bound proteins. GP-containing fractions elute between 0.1–0.2 M NaCl range, as detected by monitoring the eluant for peak protein absorbance at $A_{280}$. The GP protein is then identified by visualizing the $M_r$ approximately 97 kdal GP protein band by sodium dodecyl sulfate polyacrylamide gel electrophoresis (SDS-PAGE) followed by silver staining (2D-silver Stain II "Daiichi Kit", Daiichi Pure Chemicals Co., LTD., Tokyo, Japan) and then pooled. The pooled GP is dialyzed into 25 mM N,N-bis-(2-hydroxyethyl)-2-aminoethanesulfonic acid (BES), 1.0 mM DTT, 0.5 mM EDTA, 5 mM NaCl, pH 6.8 buffer and stored on ice until use.

Determination of GP Enzyme Activity

A) Activation of GP: Conversion of GPb to GPa

Prior to the determination of GP enzyme activity, the enzyme is converted from the inactive form as expressed in *E. coli* strain XL-1 Blue (designated GPb) (Stragene Cloning Systems, La Jolla, Calif.), to the active form (designated GPa) by phosphorylation of GP using phosphorylase kinase as follows. The fraction of inactive enzyme as expressed in Sf9 cells (designated GPb) is also converted to the active form (designated GPa) by the following procedure.

GP reaction with Immobilized Phosphorylase Kinase

Phosphorylase kinase (Sigma Chemical Company, St. Louis, Mo.) is immobilized on Affi-Gel® (BioRad Corp., Melvile, N.Y.) as per the manufacturer's instructions. In brief, the phosphorylase kinase enzyme (10 mg) is incubated with washed Affi-Gel® beads (1 ml) in 2.5 ml of 100 mM HEPES and 80 mM $CaCl_2$ at pH 7.4 for 4 hours at 4° C. The Affi-Gel® beads are then washed once with the same buffer prior to blocking with 50 mM HEPES and 1 M glycine methyl ester at pH 8.0 for one hour at room temperature. Blocking buffer is removed and replaced with 50 mM HEPES (pH 7.4), 1 mM β-mercaptoethanol and 0.2% $NaN_3$ for storage. Prior to use to convert GPb to GPa, the Affi-Gel® immobilized phosphorylase kinase beads are equilibrated by washing in the buffer used to perform the kinase reaction, consisting of 25 mM β-glycerophosphate, 0.3 mM DTT, and 0.3mM EDTA at pH 7.8 (kinase assay buffer).

The partially purified, inactive GPb obtained from 5'-AMP-Sepharose chromatography above (from *E. coli*) or the mixture of GPa and GPb obtained from IMAC above (from Sf9 cells) is diluted 1:10 with the kinase assay buffer then mixed with the aforementioned phosphorylase kinase enzyme immobilized on the Affi-Gel® beads. NaATP is added to 5 mM and $MgCl_2$ to 6 mM. The resulting mixture is mixed gently at 25° C. for 30 to 60 minutes. The activated sample is removed from the beads and the percent activation of GPb by conversion to GPa is estimated by determining GP enzyme activity in the presence and absence of 3.3 mM AMP. The percentage of total GP enzyme activity due to GPa enzyme activity (AMP-independent) is then calculated as follows:

$$\% \text{ of total } HLGPa = \frac{HLGP \text{ activity} - AMP}{HLGP \text{ activity} + AMP}$$

Alternately, the conversion of GPb to GPa can be monitored by isoelectric focusing, based on the shift in electrophoretic mobility that is noted following conversion of GPb to GPa. GP samples are analyzed by isoelectric focusing (IEF) utilizing the Pharmacia PfastGel System (Pharmacia Biotech. Inc., Piscataway, N.J.) using precast gels (pI range 4–6.5) and the manufacturer's recommended method. The resolved GPa and GPb bands are then visualized on the gels by silver staining (2D-silver Stain II "Daiichi Kit", Daiichi Pure Chemicals Co., LTD., Tokyo, Japan). Identification of GPa and GPb is made by comparison to *E. coli* derived GPa and GPb standards that are run in parallel on the same gels as the experimental samples.

B) GPa Activity Assay

The disease/condition treating activities described herein of the compounds of the present invention can be indirectly determined by assessing the effect of the compounds of this invention on the activity of the activated form of glycogen phosphorylase (GPa) by one of two methods; glycogen phosphorylase a activity is measured in the forward direction by monitoring the production of glucose-1-phosphate from glycogen or by following the reverse reaction, measuring glycogen synthesis from glucose-1-phosphate by the release of inorganic phosphate. All reactions are run in triplicate in 96-well microtiter plates and the change in absorbance due to formation of the reaction product is measured at the wavelength specified below in a MCC/340 MKII Elisa Reader (Lab Systems, Finland), connected to a Titertech Microplate Stacker (ICN Biomedical Co, Huntsville, Ala.).

To measure the GPa enzyme activity in the forward direction, the production of glucose-1-phosphate from glycogen is monitored by the multienzyme coupled general method of Pesce et al. [Pesce, M. A., Bodourian, S. H., Harris, R. C. and Nicholson, J. F. *Clinical Chemistry* 23: 1711–1717 (1977)] modified as follows: 1 to 100 μg GPa, 10 units phosphoglucomutase and 15 units glucose-6-phosphate dehydrogenase (Boehringer Mannheim Biochemicals, Indianapolis, Ind.) are diluted to 1 mL in Buffer D (pH 7.2, 50 mM HEPES, 100 mM KCl, 2.5 mM ethyleneglycoltetraacetic acid (EGTA), 2.5 mM $MgCl_2$, 3.5 mM $KH_2PO_4$ and 0.5 mM dithiothreitol). Twenty μl of this stock is added to 80 μl of Buffer D containing 0.47 mg/mL glycogen, 9.4 mM glucose, 0.63 mM of the oxidized form of nicotinamide adenine dinucleotide phosphate (NADP+). The compound to be tested is added as 5 μl of solution in 14% dimethylsulfoxide (DMSO) prior to the addition of the enzymes. The basal rate of GPa enzyme activity in the absence of inhibitors, e.g., a compound of this invention, is determined by adding 5 μl of 14% DMSO and a fully-inhibited rate of GPa enzyme activity is obtained by adding 20 μl of 50 mM of the positive control test substance, caffeine. The reaction is followed at room temperature by measuring the conversion of oxidized NADP+ to reduced NADPH at 340 nm.

To measure the GPa enzyme activity in the reverse direction, the conversion of glucose-1-phosphate into glycogen plus inorganic phosphate is measured by the general method described by Engers et al. [Engers, H. D., Shechosky, S. and Madsen, N. B., *Can. J. Biochem.* 48: 746–754 (1970)] modified as follows: 1 to 100 μg GPa is diluted to 1 ml in Buffer E (pH 7.2, 50 mM HEPES, 100 mM KCl, 2.5 mM EGTA, 2.5 mM $MgCl_2$ and 0.5 mM dithiothreitol). Twenty μl of this stock is added to 80 μl of Buffer E with 1.25 mg/ml glycogen, 9.4 mM glucose, and 0.63 mM glucose-1-phosphate. The compound to be tested is added as 5 μl of solution in 14% DMSO prior to the addition of the enzyme. The basal rate of GPa enzyme activity in the absence of added inhibitors, e.g., a compound of this invention, is determined by adding 5 μl of 14% DMSO and a fully-inhibited rate of GPa enzyme activity is obtained by adding 20 μL of 50 mM caffeine. This mixture is incubated at room temperature for 1 hour and the inorganic phosphate released from the glucose-1-phosphate is measured by the general method of Lanzetta et al. [Lanzefta, P. A., Alvarez, L. J., Reinach, P. S. and Candia, O. A. Anal. Biochem. 100: 95–97 (1979)] modified as follows: 150 µl of 10 mg/ml ammonium molybdate, 0.38 mg/ml malachite green in 1 N HCl is added to 100 µl of the enzyme mix. After a 20 minute incubation at room temperature, the absorbance is measured at 620 nm.

The above assays carried out with a range of concentrations of test compound allows the determination of an $IC_{50}$ value (concentration of test compound required for 50% inhibition) for the in vitro inhibition of GPa enzyme activity by that test compound.

Animal Models

Experimental models for the study of the treatment of diabetic cardiomyopathy include the streptozocin-induced diabetic rat with one-clip renal hypertension, or the Syrian hamster, a hereditary model of congestive cardiomyopathy, as referenced in Nagano, M., and Dhalla, N. S. *The Diabetic Heart*. Raven Press, NY 1991, pages 94–96. In general, for studies conducted in the streptozocin-diabetic rat with one-clip renal hypertension, rats are either left untreated, or treated with the glycogen phosphorylase inhibitor (GPI) for up to 7 months. Effects on diabetic cardiomyopathy can be determined by comparing the GPI treated group with the untreated group and looking for improvement in the following parameters: mortality rate, lung edema (as marker of congestive heart failure), myocarial fibrosis, contractile function of the papillary muscles, and histologic myocardial tissue markers of diabetic cardiomyopathy such as infarction, small vessel damage (microangiopathy), reperfusion necrosis, scarring, tortuosity, focal constrictions, and microaneurysms. A positive effect of the GPI treatment can be identified by a statistically significant difference between the GPI treated and the untreated group. Methods for performing these analyses are well known to those skilled in the art. See, for example, Nagano, M., and Dhalla, N. S., *The Diabetic Heart*, Raven Press, NY 1991, pages 94–96.

In Vivo Experiments

The in vivo utility of glycogen phosphorylase inhibitors in the treatment of human diabetic cardiomyopathy can be demonstrated using a randomized, double-blind, placebo-controlled clinical trial.

In the study, both male and female patients between 18 and 65 years of age who demonstrate diabetes mellitus as defined by World Health Organization criteria (W.H.O. 1980/85 Technical Report Series No. 646/727) are initially evaluated for evidence of impaired cardiac performance indicative of diabetic cardiomyopathy.

Accordingly, a placebo-controlled, single-blind baseline evaluation is performed on prospective patients over a four week period utilizing the determination of heart rate variability during controlled respiration, and during a Valsalva test, and radionuclide ventriculography using multi-gated acquisition (MUGA) methodology (B. L. Holman, *Heart Disease*, 3rd Edition, Chapter 11).

Radioventriculogram (RVG) determinations are made at rest, and during selected stages of exertion using a bicycle system suitable for use during ventriculography. Indicators of greatest importance are those involving rate of filling into and ejection of blood from the left ventricle, systolic and end diastolic volume of the left ventricle, calculated stroke volume, ejection fraction and cardiac output. The assessment of left ventricular volumes adds important complimentary information to the measurement of systolic and diastolic function. Absolute ventricular volumes are calculated according to the method of Massardo, et. al., *J. Nucl. Med.*, Vol. 31, pp. 450–456, 1990. To be admitted into the double-blind phase, each patient must demonstrate either a peak filling rate below 3 EDV (End Diastolic Volume)/sec, resting systolic ejection fraction (EF) below 50% of EDV, or a subnormal increase in left ventricular ejection fraction between resting and maximal level of exertion. It is noted that these are the current diagnostic criteria, which may be revised in the future. It is intended that the present methods track the most current diagnostic criteria.

The degree of impairment of cardiac autonomic activity may be shown by a reduction in the normal variability of EKG R-R interval, most obviously, during respiration. The standard deviation of the mean R-R interval for a five-minute period during quiet breathing is a commonly used method of determining R-R variation, which is primarily a measure of parasympathetic nervous system activity. See, for example, T. Roy, et. al., *Am. J. Med.*, Vol. 87, pp. 382–388, 1989. The Valsalva test (Gorlin, et. al., *Am. J. Med.*, Vol. 22, pp. 197–203, 1957) is a cardiovascular test that relies upon evaluation of cardiac responses during and after a standardized increase in intrathoracic pressure (Valsalva maneuver). An abnormally low Valsalva ratio (the fastest heart rate during the Valsalva maneuver divided by the slowest heart rate after the Valsalva maneuver) may be due either to decreased cardiac parasympathetic or decreased cardiac or vascular sympathetic tone. Thus, it serves as a general autonomic test.

A stress thallium test is also performed with concurrent determination of EKG changes to preclude participation of any patient presenting unequivocal evidence of coronary artery disease. Prospective patients exhibiting such evidence are withdrawn from the study.

The single-blind placebo baseline evaluation is followed by a double-blind period of 52 weeks duration during which patients are randomly assigned to a treatment regimen consisting of either placebo or gylcogen phosphorylase inhibitor. It is noted that the study can be designed to test more than one glycogen phosphorylase dosage.

The evaluation of cardiac performance endpoints as determined by radionuclide ventriculography is conducted at weeks 4 and 16 and at week 52 of the double-blind period.

What is claimed is:

1. A method of treating diabetic cardiomyopathy, the method comprising administering to a diabetic patient having or at risk of having diabetic cardiomyopathy a therapeutically effective amount of a glycogen phosphorylase inhibitor selected from the group consisting of 5-chloro-1H-indole-2-carboxylic acid [(1S)-((R)-hydroxy-dimethylcarbamoyl-methyl)-2-phenyl-ethyl]-amide; 5,6-dichloro-1H-indole-2-carboxylic acid {(1S)-[(R)-hydroxy-(methoxy-methyl-carbamoyl)-methyl]-2-phenyl-ethyl}-amide; 5-chloro-1H-indole-2-carboxylic acid {(1S)-[(R)-hydroxy-(methoxy-methyl-carbamoyl)-methyl]-2-phenyl-eth-yl}-amide; 5-chloro-1H-indole-2-carboxylic acid ((1S)-{(R)-hydroxy-[(2-hydroxy-ethyl)-methyl-carbamoyl]-methyl}-2-phenyl-ethyl)-amide; 5-chloro-1H-indole-2-carboxylic acid [(1S)-benzyl-3-((3R,4S)-dihydroxy-pyrrolidin-1-yl)-(2R)-hydroxy-3-oxo-propyl]-amide; 5-chloro-1H-indole-2-carboxylic acid {(1S)-[(R)-hydroxy-(methyl-pyridin-2-yl-carbamoyl)-methyl]-2-phenyl-ethyl}-amide; or 5-chloro-1H-indole-2-carboxylic acid ((1S)-{(R)-hydroxy-[methyl-(2-pyridin-2-yl-ethyl)-carbamoyl]-methyl}-2-phenyl-ethyl)-amide, or a pharmaceutically acceptable salt or prodrug thereof, or a salt of a prodrug.

2. The method of claim 1, comprising administering to a diabetic patient having cardiovascular disease, ischemic heart disease, hypertension, diastolic blood pressure abnormalities, microvascular diabetic complications, abnormal left ventricular function, myocardial fibrosis, abnormal cardiac function, pulmonary congestion, small vessel disease, small vessel disease without atherosclerotic cardiovascular disease or luminal narrowing, coagulopathy, cardiac contusion, congestive heart failure, congestive heart failure without coronary arteriosclerosis, or having had or at risk of having a myocardial infarction a therapeutically effective amount of a glycogen phosphorylase inhibitor.

3. A method of treating or decreasing injury to the myocardium, the method comprising administering to a diabetic patient who is at risk of suffering myocardial ischemia and reperfusion a therapeutically effective amount of a glycogen phosphorylase inhibitor selected from the group consisting of 5-chloro-1H-indole-2-carboxylic acid [(1S)-((R)-hydroxy-dimethylcarbamoyl-methyl)-2-phenyl-ethyl]-amide; 5,6-dichloro-1H-indole-2-carboxylic acid {(1S)-[(R)-hydroxy-(methoxy-methyl-carbamoyl)-methyl]-2-phenyl-ethyl}-amide; 5-chloro-1H-indole-2-carboxylic acid {(1S)-[(R)-hydroxy-(methoxy-methyl-carbamoyl)-methyl]-2-phenyl-ethyl}-amide; 5-chloro-1H-indole-2-carboxylic acid ((1S)-{(R)-hydroxy-[(2-hydroxy-ethyl)-methyl-carbamoyl]-methyl}-2-phenyl-ethyl)-amide; 5-chloro-1H-indole-2-carboxylic acid [(1S)-benzyl-3-((3R,4S)-dihydroxy-pyrrolidin-1-yl)-(2R)-hydroxy-3-oxo-propyl]-amide; 5-chloro-1H-indole-2-carboxylic acid {(1S)-[(R)-hydroxy-(methyl-pyridin-2-yl-carbamoyl)-methyl]-2-phenyl-ethyl}-amide; or 5-chloro-1H-indole-2-carboxylic acid ((1S)-{(R)-hydroxy-[methyl-(2-pyridin-2-yl-ethyl)-carbamoyl]-methyl}-2-phenyl-ethyl)-amide, or a pharmaceutically acceptable salt or prodrug thereof, or a salt of a prodrug.

4. The method of claim 3 wherein the diabetic patient is at risk of suffering myocardial isehemia and reperfusion as a result of having to undergo a balloon angioplasty.

5. The method of claim 3 wherein the diabetic patient is at risk of suffering myocardial isehemia and reperfusion as a result of having to undergo bypass surgery.

6. The method of claim 3 wherein the diabetic patient is at risk of suffering myocardial ischemia and reperfusion as a result of having to undergo major non-cardiac surgery.

7. A method of treating or delaying the onset of diabetic cardiomyopathy, the method comprising administering to a patient newly diagnosed as having diabetes a therapeutically effective amount of a glycogen phosphorylase inhibitor selected from the group consisting of 5-chloro-1H-indole-2-carboxylic acid [(1S)-(R)-hydroxy-dimethylcarbamoyl-methyl)-2-phenyl-ethyl]-amide; 5,6-dichloro-1H-indole-2-carboxylic acid {(1S)-[(R)-hydroxy-(methoxy-methyl-carbamoyl)-methyl]-2-phenyl-ethyl}-amide; 5-chloro-1H-indole-2-carboxylic acid {(1S)-[(R)-hydroxy-(methoxy-methyl-carbamoyl)-methyl]-2-phenyl-ethyl}-amide; 5-chloro-1H-indole-2-carboxylic acid ((1S)-{(R)-hydroxy-[(2-hydroxy-ethyl)-methyl-carbamoyl]-methyl}-2-phenyl-ethyl)-amide; 5-chloro-1H-indole-2-carboxylic acid [(1S)-benzyl-3-((3R,4S)-dihydroxy-pyrrolidin-1-yl)-(2R)-hydroxy-3-oxo-propyl]-amide; 5-chloro-1H-indole-2-carboxylic acid {(1S)-[(R)-hydroxy-(methyl-pyridin-2-yl-carbamoyl)-methyl]-2-phenyl-ethyl}-amide; or 5-chloro-1H-indole-2-carboxylic acid ((1S)-{(R)-hydroxy-[methyl-(2-pyridin-2-yl-ethyl)-carbamoyl]-methyl}-2-phenyl-ethyl)-amide, or a pharmaceutically acceptable salt or prodrug thereof, or a salt of a prodrug.

8. A method of treating diabetic cardiomyopathy, the method comprising administering to a diabetic patient having or at risk of having diabetic cardiomyopathy a therapeutically effective amount of a glycogen phosphorylase inhibitor selected from the group consisting of 5-chloro-1H-indole-2-carboxylic acid [(1S)-((R)-hydroxy-dimethylcarbamoyl-methyl)-2-phenyl-ethyl]-amide; 5,6-dichloro-1H-indole-2-carboxylic acid {(1S)-[(R)-hydroxy-(methoxy-methyl-carbamoyl)-methyl]-2-phenyl-ethyl}-amide; 5-chloro-1H-indole-2-carboxylic acid {(1S)-[(R)-hydroxy-(methoxy-methyl-carbamoyl)-methyl]-2-phenyl-ethyl}-amide; 5-chloro-1H-indole-2-carboxylic acid ((1S)-{(R)-hydroxy-[(2-hydroxy-ethyl)-methyl-carbamoyl]-methyl}-2-phenyl-ethyl)-amide; 5-chloro-1H-indole-2-carboxylic acid [(1S)-benzyl-3-((3R,4S)-dihydroxy-pyrrolidin-1-yl)-(2R)-hydroxy-3-oxo-propyl]-amide; 5-chloro-1H-indole-2-carboxylic acid {(1S)-[(R)-hydroxy-(methyl-pyridin-2-yl-carbamoyl)-methyl]-2-phenyl-ethyl}-amide; or 5-chloro-1H-indole-2-carboxylic acid ((1S)-{(R)-hydroxy-[methyl-(2-pyridin-2-yl-ethyl)-carbamoyl]-methyl}-2-phenyl-ethyl)-amide, or a pharmaceutically acceptable salt or prodrug thereof, or a salt of a prodrug in combination with an additional compound, the additional compound being useful to treat diabetes, cardiovascular disease, ischemic heart disease, congestive heart failure, hypertension, diastolic blood pressure abnormalities, microvascular diabetic complications, abnormal left ventricular function, myocardial fibrosis, abnormal cardiac function, pulmonary congestion, small vessel disease, coagulopathy, cardiac contusion, or myocardial infarction.

9. The method claim 8 wherein the additional compound is selected from insulin, insulin analogs, biguanides, alpha.2-antagonists, and imidazolines, glitazones, PPAR-gamma agonists, fatty acid oxidation inhibitors, alpha.-glucosidase inhibitors, beta-agonists, phosphodiesterase inhibitors, lipid-lowering agents, antiobesity agents, vanadate, vanadium, and peroxovanadium complexes, amylin antagonists, glucagon antagonists, gluconeogenesis inhibitors, somatostatin analogs and antagonists, or antilipolytic agents.

10. The method of claim 8 wherein the additional compound is selected from an aldose reductase inhibitor; a glucocorticoid receptor antagonist; a sodium-hydrogen exchanger type 1 inhibitor; or a thyromimetic.

* * * * *